US005830849A

United States Patent [19]
Dixon et al.

[11] Patent Number: 5,830,849

[45] Date of Patent: Nov. 3, 1998

[54] VAMPIRE BAT SALIVARY PLASMINOGEN ACTIVATORS

[75] Inventors: Richard A. F. Dixon, Lansdale; Stephen J. Gardell, North Wales; Le Thi Duong, Jenkintown; Paul A. Friedman, Rosemont; John W. Jacobs, Doylestown, all of Pa.; George E. Mark, Princeton Junction; Bruce L. Daugherty, South Orange, both of N.J.

[73] Assignee: Schering Aktiengesellschaft, Berlin, Germany

[21] Appl. No.: 467,966

[22] Filed: Jun. 6, 1995

Related U.S. Application Data

[63] Continuation of Ser. No. 870,170, Apr. 16, 1992, abandoned, which is a continuation of Ser. No. 784,102, Oct. 28, 1991, abandoned, which is a continuation of Ser. No. 377,221, Jul. 13, 1989, abandoned, which is a continuation-in-part of Ser. No. 221,697, Jul. 20, 1988, abandoned.

[51] Int. Cl.[6] .............................. C12N 1/21; C12N 15/12; C12N 9/64; A61K 38/43

[52] U.S. Cl. .............................. 514/2; 435/69.1; 435/226; 435/252.3; 435/320.1; 435/325; 435/172.3; 530/395; 536/23.2; 536/23.5

[58] Field of Search .............................. 435/320.1, 172.3, 435/226, 69.1, 252.3, 325; 536/23.2, 23.5; 530/395; 514/2

[56] References Cited

U.S. PATENT DOCUMENTS

| | | | |
|---|---|---|---|
| 4,766,075 | 8/1988 | Goeddel et al. | 435/369 |
| 5,010,002 | 4/1991 | Levinson et al. | 435/69.2 |

FOREIGN PATENT DOCUMENTS

| | | |
|---|---|---|
| 311589 | 4/1989 | European Pat. Off. . |
| 383417 | 8/1990 | European Pat. Off. . |
| WO 87/05934 | 10/1987 | WIPO . |

OTHER PUBLICATIONS

Romma, Bulletin de la Societe de Pathologie Exotique, vol. 32, pp. 399–403 (1939).

DiSanto,J. Morphol., vol. 106, pp. 301–335 (1960).

Hawkey, Nature, vol. 211, pp. 434–435 (1966).

Hawkey, Brit. J. Haemat., vol. 13, pp. 1014–1020 (1967).

Cartwright, Blood, vol. 43, No. 3, pp. 317–326 (1974).

Stamp, et al.,J. Bio. Chem. vol. 261, No. 36, pp. 17120–17126 (1986).

Gheyson, et al.,J. Biol. Chem., vol. 262, No. 24, pp. 11779–11784 (1987).

Gething, et al. EMBO Journal, vol. 7, No. 9, pp. 2731–2740 (1988).

van Zonnevield, et al., Proc. Natl. Acad. Sc. USA, vol. 83, pp. 4670–4674 (1986).

*Primary Examiner*—George C. Elliott
*Assistant Examiner*—Johnny F Railey, II
*Attorney, Agent, or Firm*—Millen, White, Zelano, & Branigan, P.C.

[57] ABSTRACT

Purified plasminogen activator proteins obtained or derived from the vampire bat *Desmodus rotundus* saliva and salivary glands, methods for purifying the proteins, DNA sequences encoding these proteins, means for producing them using recombinant DNA technology, pharmaceutical compositions comprising these proteins and methods of treatment utilizing these proteins are provided.

38 Claims, 14 Drawing Sheets

* PLASMINOGEN ACTIVATOR "L" HAS PROLINE PRESENT AT POSITION 88 RATHER THAN THREONINE.

```
-90   ACCCAATTCGCGCAAGAGCTGAGCTGACGGGAAATCCTCTCCAGGAGAGAAGGAAGGCAAGGAGTGGCGAGTTTAAGGGACACCGCAGAA
1     ATGGTGAATACAATGAAGACAAAGCTGTTGTGTGTACTGCTGCTTTGTGGAGCAGTCTTCTCGTTGCCCAGGCAGGAAACCTACAGGCAA
(-36) M  V  N  T  M  K  T  K  L  L  C  V  L  L  L  C  G  A  V  F  S  L  P  R  Q  E  T  Y  R  Q   (-07)
91    TTGGCAAGGGGATCCAGAGCATATGGTGTGGCCTGCAGAGACGAAAAAACCCAGATGATATACCAGCAACAAGAGTCGTGGCTGCGCCCC
      L  A  R  G  S  R  A  Y  G  V  A  C  R  D  E  K  T  Q  M  I  Y  Q  Q  Q  E  S  W  L  R  P     24
181   GAGGTCAGAAGCAAGCGGGTAGAACACTGCCGGTGCGATAGAGGATTGGCCCAGTGTCACACCGTGCCTGTCAAAAGTTGCAGTGAACTG
      E  V  R  S  K  R  V  E  H  C  R  C  D  R  G  L  A  Q  C  H  T  V  P  V  K  S  C  S  E  L     54
271   AGGTGCTTCAATGGGGGGACATGCTGGCAGGCTGCATCTTTCTCAGACTTTGTCTGTCAGTGCCCTAAAGGATATACGGGGAAACAGTGT
      R  C  F  N  G  G  T  C  W  Q  A  A  S  F  S  D  F  V  C  Q  C  P  K  G  Y  T  G  K  Q  C     84
361   GAAGTAGATACCCATGCCACCTGCTACAAGGACCAGGGTGTCACCTACAGGGGCACATGGAGCACATCGGAAAGTGGGGCTCAGTGTATC
      E  V  D (T)*H  A  T  C  Y  K  D  Q  G  V  T  Y  R  G  T  W  S  T  S  E  S  G  A  Q  C  I    114
451   AACTGGAACAGCAACCTTCTGACCCGGAGGACCTACAATGGGCGGAGGTCAGATGCCATCACACTGGGCCTTGGGAATCACAATTACTGC
      N  W  N  S  N  L  L  T  R  R  T  Y  N  G  R  R  S  D  A  I  T  L  G  L  G  N  H  N  Y  C    144
541   AGAAACCCAGATAACAACTCAAAACCTTGGTGCTATGTCATCAAGGCAAGCAAGTTCATCTTGGAGTTCTGTAGCGTGCCTGTCTGCTCC
      R  N  P  D [N] N  S  K  P  W  C  Y  V  I  K  A  S  K  F  I  L  E  F  C  S  V  P  V  C  S    174
631   AAGGCCACCTGTGGCCTGAGAAAGTACAAGGAGCCACAGCTTCACAGTACAGGAGGACTCTTCACAGACATCACCTCTCATCCATGGCAG
      K  A  T  C  G  L  R  K  Y  K  E  P  Q  L  H  S  T  G  G  L  F  T  D  I  T  S  H  P  W  Q    204
```

FIG. 8A-1

```
721   GCTGCCATCTTTGCCCAGAACAGAAGGTCATCAGGAGAAAGGTTCTTGTGTGGGGGATATTGATCAGTTCCTGCTGGGTCCTGACTGCT
      A  A  I  F  A  Q  N  R  R  S  S  G  E  R  F  L  C  G  G  I  L  I  S  S  C  W  V  L  T  A     234
811   GCCCACTGCTTCCAGGAGAGGTATCCTCCCCAGCATCTTAGGGTGGTTTTGGGCAGAACATACCGGGTGAAACCTGGAAAGGAAGAGCAG
      A  H  C  F  Q  E  R  Y  P  P  Q  H  L  R  V  V  L  G  R  T  Y  R  V  K  P  G  K  E  E  Q     264
901   ACATTTGAAGTCGAAAAATGCATCGTCCATGAGGAATTTGATGACGACACTTACAACAATGACATTGCACTGCTGCAGCTGAAATCGGGC
      T  F  E  V  E  K  C  I  V  H  E  E  F  D  D  D  T  Y  N  N  D  I  A  L  L  Q  L  K  S  G     294
991   TCGCCACAGTGTGCCCAAGAGAGTGACAGTGTCCGCGCCATCTGTCTCCCGGAAGCCAACCTGCAGCTGCCCGACTGGACAGAATGTGAG
      S  P  Q  C  A  Q  E  S  D  S  V  R  A  I  C  L  P  E |A  N  L  Q  L  P  D  W  T  E  C  E     324
                                                           V-2
1081  CTGTCTGGCTACGGCAAGCATAAGTCATCTTCTCCTTTCTATTCTGAGCAGCTGAAGGAAGGGCATGTCAGGCTGTACCCCTCCAGCCGC
      L  S  G  Y  G  K  H  K  S  S  S  P  F  Y  S  E  Q  L  K  E  G  H  V  R  L  Y  P  S  S  R     354
1171  TGCACATCCAAGTTTCTGTTTAACAAAAACCGTCACAAAGAACATGCTGTGTGCTGGAGACACGCGGAGCGGAGAGATCCATCCAAATGTG
      C  T  S  K  F  L  F [N] K  T  V  T  K  N  M  L  C  A  G  D  T  R |S  G  E  I  H  P  N  V     384
                                                                      T-1
1261  CACGATGCCTGCCAGGGTGACTCAGGAGGCCCCTTGGTGTGTAGGAATGACAACCACATGACTTTGCTTGGCATCATCAGTTGGGGTGTT
      H  D  A  C  Q  G  D  S  G  G  P  L  V  C  R  N  D  N  H  M  T  L  L  G  I  I  S  W  G  V     414
                         *
1351  GGCTGTGGGGAGAAAGACATTCCAGGTGTATACACCAAGGTTACTAATTACCTAGGCTGGATTCGAGACAACATGCGCCCATAACCAAGA
      G  C  G  E  K  D  I  P  G  V  Y  T  K  V  T  N  Y  L  G  W  I  R  D  N  M  R  P           441
1441  ACACGCAACTCCCTGGCAGCCCCTGCCTTCCTCCACCCCAGAAGAAACACAAGGCAGAATGCTTCCTGACACCAGTTTCTTCACAAGCCT
```

FIG. 8A-2

VAMPIRE BAT SALIVARY PLASMINOGEN ACTIVATORS

CROSS-REFERENCE

This is a continuation of the application Ser. No. 07/870,170 filed 16 Apr. 1992, abandoned, which is a continuation of application Ser. No. 07/784,102 filed 28 Oct. 1991, abandoned, which is a continuation of Ser. No. 07/377,221 filed 13 Jul. 1989, abandoned, which is a continuation-in-part of application Ser. No. 07/221,697 filed 20 Jul. 1988, also abandoned.

BACKGROUND OF THE INVENTION

Vampire bats are absolutely dependent on a diet of fresh blood which they obtain by inflicting a wound on their victim. These wounds, although superficial, continue to ooze blood for a period of several hours.

Components of vampire bat saliva of *Desmodus rotundus* were studied and shown to interfere with the hemostatic mechanism of mammalian blood at three distinct levels. They were shown to inhibit platelet aggregation and activate plasminogen (Hawkey, C. M. *Nature* 211:434 (1966) and Hawkey, C. M. *Br. J. Haematol.* 13:1014 (1967)). Each of these activities was associated with a distinct protein fraction. The fraction which activated plasminogen was named "desmokinase" (Hawkey, C. M., *Nature*). Cartwright, T., *Blood,* describes the purification of desmokinase from Desmodus saliva, and suggested it is more effective than urokinase (UK) and streptokinase in lysis of preformed clots.

The use of tissue-type plasminogen activator (tPA) as a thrombolytic agent is beset by a number of drawbacks, including serious bleeding complications, a relatively frequent incidence of reocclusion, an inability to be uniformly effective, and susceptibility to inactivation by plasminogen activator inhibitors such as Type 1 plasminogen activator inhibitor (PAI-1) (Loskutoff, *Seminars in Thrombosis and Hemostasis,* Vol. 14, No. 1 (1988)).

Bleeding complications which result from thrombolytic therapy are believed to be caused or, at least, exacerbated by the activation of circulating plasminogen. The ability of tPA to bind to fibrin is thought to be responsible for its marked substrate preference towards fibrin-bound plasminogen. Nevertheless, theoretical considerations and the results of clinical studies have shown that the elevated levels of tPA required for rapid clot dissolution also cause activation of appreciable amounts of circulating plasminogen.

Furthermore, it is believed that interactions of tPA with plasma inhibitors attenuate functional activity of tPA during and after infusion, thereby potentially contributing to reocclusion.

An additional drawback which accompanies the use of tPA as a thrombolytic agent is that the required dose of tPA is large, between 100 and 150 mg, which makes this therapeutic intervention extremely expensive.

We have found plasminogen activators present in *Desmodus rotundus* saliva and salivary glands that exhibit remarkable greater selectivity towards fibrin-bound plasminogen and hence, may be associated with decreased severity and frequency of bleeding diathesis when used for thrombolytic therapy. Furthermore, the activators are not readily inactivated by plasma inhibitors such as PAI-1, and, hence, may be associated with a lower frequency of reocclusion.

It is a purpose of the present invention to provide fibrinolytic agents which are superior to tPA with respect to both safety and efficacy.

It is also a purpose of the present invention to identify DNA sequences encoding proteins of the present invention, fashion the sequences from tissue derived cDNA, and operably insert the sequences into expression vectors.

It is also a purpose of the present invention to produce proteins of the present invention from host microorganisms or eucaryotic cells which have been transformed by expression vectors to produce the protein.

It is also a purpose of the present invention to produce antibodies reactive against proteins of the present invention.

SUMMARY OF THE INVENTION

The invention includes purified and partially purified plasminogen activator proteins obtained or derived from *Desmodus rotundus* saliva and salivary glands, methods for purifying the proteins from vampire bat *Desmodus rotundus* saliva and salivary glands, DNA sequences encoding these proteins, means for producing them using recombinant DNA methodology, antibodies specifically reactive with these proteins, and pharmaceutical compositions for activating fibrin-bound plasminogen comprising proteins of the invention.

The protein plasminogen activators isolated from vampire bat saliva and salivary glands are distinct from both tPA and urokinase by several structural and functional criteria. Unlike tPA, plasminogen activators of the invention do not contain the kringle 2 domain and plasmin-sensitive processing site. Equimolar quantities of these activators and tPA are similarity efficacious when monitored for their abilities to catalyze lysis of preformed plasma clots. Their activity towards plasminogen is stimulated at least 27,000-fold in the presence of a fibrin cofactor. The corresponding value for tPA is only 205-fold. Three distinct species corresponding to full-length, finger-minus and finger EGF-minus forms of tPA have been isolated from vampire bat saliva. They are referred to as Bat-PA(H), Bat-PA(I), and Bat-PA(L), respectively. References hereinafter to "Bat-PA" correspond to the unfractionated preparation containing the three molecular forms H, I and L. The full-length species, unlike the other two, binds tightly to fibrin. Bat-PA(H), Bat-PA(I), and Bat-PA(L) exhibit $M_r$ values of 49, 42 and 40 kD, respectively, as determined by SDS-PAGE in the presence of dithiothreitol (FIG. 1, lane 1). The apparent $M_r$ values of the deglycosylated forms of Bat-PA(H), Bat-PA(I) and Bat-PA (L) (obtained by removing the N-linked carbohydrate chains with endoglycosidase F), as determined by SDS-PAGE are 44, 40 and 38 kD respectively (FIG. 1, lane 2). These proteins exhibit a stringent requirement for the presence of a fibrin cofactor and a remarkable ability to catalyze the lysis of plasma clots. The mechanism for the selectivity of these proteins towards fibrin-bound plasminogen is a result of several factors including direct fibrin binding and potent inhibition by NaCl which is relieved in the presence of the fibrin clot. Furthermore, the vampire bat plasminogen activators are less susceptible than tPA to inactivation by inhibitors present in plasma.

The amino acid sequence predicted from the cDNA of the "full-length" glycoprotein plasminogen activator (Bat-PA (H)) derived from *Desmodus rotundus* saliva is:

Ala-Tyr-Gly-Val-Ala-Cys-Arg-Asp-Glu-Lys-Thr-Gln-
Met-Ile-Tyr-Gln-Gln-Gln-Glu-Ser-Trp-Leu-Arg-Pro-
Glu-Val-Arg-Ser-Lys-Arg-Val-Glu-His-Cys-Arg-Cys-
Asp-Arg-Gly-Leu-Ala-Gln-Cys-His-Thr-Val-Pro-Val-
Lys-Ser-Cys-Ser-Glu-Leu-Arg-Cys-Phe-Asn-Gly-Gly-

-continued

Thr-Cys-Trp-Gln-Ala-Ala-Ser-Phe-Ser-Asp-Phe-Val-
Cys-Gln-Cys-Pro-Lys-Gly-Tyr-Thr-Gly-Lys-Gln-Cys-
Glu-Val-Asp-Thr-His-Ala-Thr-Cys-Tyr-Lys-Asp-Gln-
Gly-Val-Thr-Tyr-Arg-Gly-Thr-Trp-Ser-Thr-Ser-Glu-
Ser-Gly-Ala-Gln-Cys-Ile-Asn-Trp-Asn-Ser-Asn-Leu-
Leu-Thr-Arg-Arg-Thr-Tyr-Asn-Gly-Arg-Arg-Ser-Asp-
Ala-Ile-Thr-Leu-Gly-Leu-Gly-Asn-His-Asn-Tyr-Cys-
Arg-Asn-Pro-Asp-Asn-Asn-Ser-Lys-Pro-Trp-Cys-Tyr-
Val-Ile-Lys-Ala-Ser-Lys-Phe-Ile-Leu-Glu-Phe-Cys-
Ser-Val-Pro-Val-Cys-Ser-Lys-Ala-Thr-Cys-Gly-Leu-
Arg-Lys-Tyr-Lys-Glu-Pro-Gln-Leu-His-Ser-Thr-Gly-
Gly-Leu-Phe-Thr-Asp-Ile-Thr-Ser-His-Pro-Trp-Gln-
Ala-Ala-Ile-Phe-Ala-Gln-Asn-Arg-Arg-Ser-Ser-Gly-
Glu-Arg-Phe-Leu-Cys-Gly-Gly-Ile-Leu-Ile-Ser-Ser-
Cys-Trp-Val-Leu-Thr-Ala-Ala-His-Cys-Phe-Gln-Glu-
Arg-Tyr-Pro-Pro-Gln-His-Leu-Arg-Val-Val-Leu-Gly-
Arg-Thr-Tyr-Arg-Val-Lys-Pro-Gly-Lys-Glu-Glu-Gln-
Thr-Phe-Glu-Val-Glu-Lys-Cys-Ile-Val-His-Glu-Glu-
Thr-Phe-Glu-Val-Glu-Lys-Cys-Ile-Val-His-Glu-Glu-
Phe-Asp-Asp-Asp-Thr-Tyr-Asn-Asn-Asp-Ile-Ala-Leu-
Leu-Gln-Leu-Lys-Ser-Gly-Ser-Pro-Gln-Cys-Ala-Gln-
Glu-Ser-Asp-Ser-Val-Arg-Ala-Ile-Cys-Leu-Pro-Glu-
Ala-Asn-Leu-Gln-Leu-Pro-Asp-Trp-Thr-Glu-Cys-Glu-
Leu-Ser-Gly-Tyr-Gly-Lys-His-Lys-Ser-Ser-Ser-Pro-
Phe-Tyr-Ser-Glu-Gln-Leu-Lys-Glu-Gly-His-Val-Arg-
Leu-Tyr-Pro-Ser-Ser-Arg-Cys-Thr-Ser-Lys-Phe-Leu-
Phe-Asn-Lys-Thr-Val-Thr-Lys-Asn-Met-Leu-Cys-Ala-
Gly-Asp-Thr-Arg-Ser-Gly-Glu-Ile-His-Pro-Asn-Val-
His-Asp-Ala-Cys-Gln-Gly-Asp-Ser-Gly-Gly-Pro-Leu-
Val-Cys-Met-Asn-Asp-Asn-His-Met-Thr-Leu-Leu-Gly-
Ile-Ile-Ser-Trp-Gly-Val-Gly-Cys-Gly-Glu-Lys-Asp-
Ile-Pro-Gly-Val-Tyr-Thr-Lys-Val-Thr-Asn-Tyr-Leu-
Gly-Trp-Ile-Arg-Asp-Asn-Met-Arg-Pro

Bat-PA(H) contains the sequence of amino acids 1–441 shown in FIG. 8*a*. Bat-PA(I) contains the sequence of amino acids 1–3 and 50–441 shown in FIG. 8*a*, and Bat-PA(L) contains the sequence of amino acids 1–3 and 87–441 shown in FIG. 8*a*. Furthermore, the amino acid at position 88 is changed from threonine to proline in protein "L".

Also within the invention is a method for purifying the vampire bat salivary plasminogen activators comprising the steps of:

(a) homogenizing submandibular glands from vampire bats to form a mixture, and centrifuging the mixture to form a supernatant fraction;

(b) applying the supernatant to a phospho-cellulose cation-exchange column which results in absorbtion of the Bat-PA to the column;

(c) eluting the column to obtain fractions containing Bat-PA;

(d) pooling the active fractions, applying the pool to an affinity chromatography column having immobilized Erythrina trypsin inhibitor (ETI) and eluting Bat-PA with low pH buffer.

Also within the present invention are DNA sequences which encode proteins of the present invention, cloning vehicles having inserted DNA sequences of the invention, antibodies reactive with proteins of the present invention, and pharmaceutical compositions for activating fibrin-bound plasminogen having effective amounts of the proteins of the invention.

Each of the plasminogen activating species is activated by fibrin. The only discernable characteristic which differentiates the species is the exclusive ability of Bat-PA(H) to bind tightly to fibrin, a property which is correlated with the presence of the Finger domain. The specificity of Bat-PA(I) and Bat-PA(L) towards fibrin-bound plasminogen appears to be independent of an ability to bind tightly to fibrin.

The strict fibrin dependence of Bat-PA activity is a characteristic which is desirable in the context of fibrinolytic therapy. Bleeding complications which accompany the use of thrombolytic agents may be exacerbated by the activation of circulating plasminogen to yield plasmin. The severity and frequency of bleeding complications can be diminished by using a plasminogen activator of the present invention whose action is localized to the site of the fibrin clot.

293-Bat-PA-1 mammalian cells (designated ATCC No. CRL 10180), BPA-CN-pSZ88-104-20 bacterial cells (designated ATCC No. 68050), BPA-CK-pSZ89-111-17 bacterial cells (designated ATCC No. 68052), BPA-FK-p89WO-1 bacterial cells (designated ATCC No. 68051), BPA-FN-p89WO-2C bacterial cells (designated ATCC No. 68053) and BPA-DK-p89WP-20A bacterial cells (designated ATCC No. 68049) have been deposited with the American Type Culture Collection, Bethesda, Md., USA, in accordance with the requirements of the Budapest Treaty. They are irrevocably available upon issuance of this patent. The deposit is also available as required by foreign patent laws in countries wherein counterparts of the subject application, or its progeny may be filed. However, it should be understood that the availability of the deposits does not constistute a license to practice the subject of the invention in derogation of patent rights granted by governmental action.

DESCRIPTION OF THE FIGURES

FIG. 8A shows nucleotide sequence of vampire bat plasminogen activator cDNA and amino acid sequences of the plasminogen activators.

Figure 12:
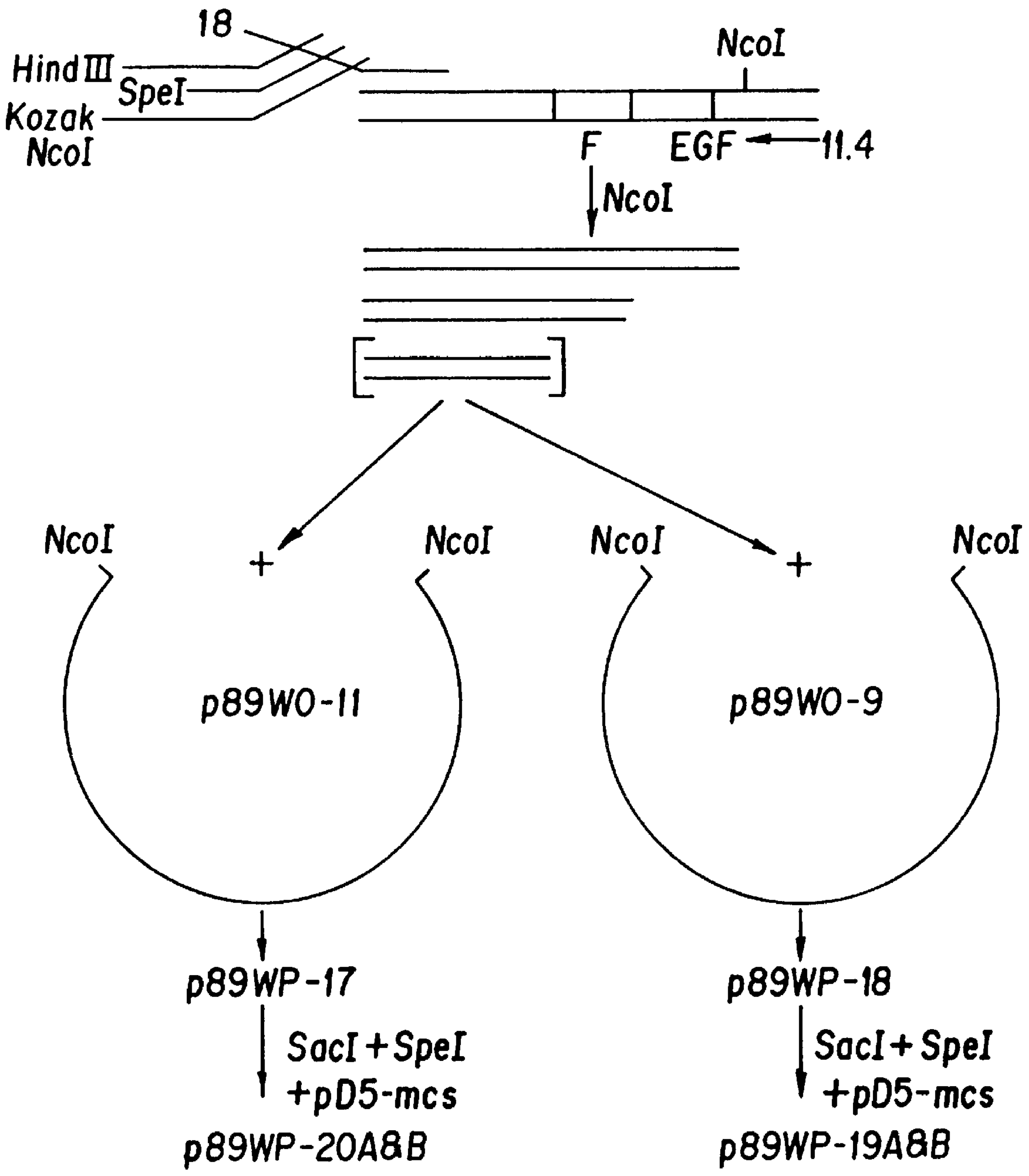

FIG. 12 depicts in schematic form the synthesis of plasmids p89WP-20A&B and p89WP-19A&B from known plasmid pD5 and p89WP-17 and p89WP-18, respectively. p89WP-17 was obtained from p89WO-11, and p89WO-18 was obtained from p89WO-9.

DETAILED DESCRIPTION OF THE INVENTION

The invention relates to native and recombinant-derived purified plasminogen activator proteins and any microheterogeneous or fragment forms of the proteins associated with vampire bat *Desmodus rotundus* saliva and salivary glands.

Protein and polypeptide are used interchangeably herein and refer to a linear polymer of amino acids bound together with amide linkages. The sequence of amino acids in the chain is of critical importance in the biological functioning of the protein or polypeptide. Plasminogen activators as used herein refers to proteins which catalyze formation of plasmin, an enzyme which hydrolyzes peptides and esters of arginine and lysine, and converts fibrin to soluble products.

Monoclonal and polyclonal antibodies for the proteins are useful for isolating and identifying proteins of the present invention. They may be produced by any of the normal techniques which are known in the art. For example, polyclonal antibodies may be synthesized by an animal, such as a rabbit, that has received an injection of the *Desmodus rotundus* plasminogen activator proteins. After injection, the antibody level in the animal rises. Antibody-containing blood, called antiserum, is then drawn from the animal. Plasminogen activator-specific antibody is then isolated from other antibodies in the antiserum, by any one of a number of separation techniques, e.g. affinity chromatography. Monoclonal antibodies may be prepared using the technique of Kohler and Milstein, *Nature,* 256, pp. 495–497 (1975).

Native proteins as used herein refers to full length proteins produced by the corresponding genes. Recombinant-derived refers to the isolation of a gene or cDNA for a desired protein and the use of that purified gene or cDNA to construct a cell which will overproduce the desired protein. Fragment forms is defined as portions of proteins or polypeptides which have fewer amino acids than the native proteins but contain the active site or sites of the plasminogen activators. Microheterogeneous forms as used herein refers to a single gene product, that is a protein produced from a single gene unit of DNA, which is structurally modified following translation. These structural modifications, however, do not result in any significant alterations of the activity of the protein. The modifications may take place either in vivo or during the isolation and purification process. In vivo modification may result in, but is not limited to, acetylation at the N-terminus, proteolysis, glycosylation or phosphorylation. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which may result in the production of microheterogeneous forms. The most common modification occuring during purification is proteolysis.

Another embodiment of the invention is a plasminogen-activating protein having a polypeptide sequence which is at least 95% homologous with the polypeptide sequence of amino acids 1–441 shown in FIG. 8*a*, said protein having plasminogen-activating activity that is stimulated in the presence of a fibrin cofactor, and said protein being capable of tightly binding to fibrin.

Another embodiment of the invention is a plasminogen-activating protein having a polypeptide sequence which is at least 90% homologous with the polypeptide sequence of amino acids 1–441 shown in FIG. 8*a*, said protein having plasminogen-activating activity that is stimulated in the presence of a fibrin cofactor, and said protein being capable of tightly binding to fibrin.

Another embodiment of the invention is a plasminogen-activating protein having a polypeptide sequence which is at least 95% homologous with the polypeptide sequence of amino acids 1–and 50–441 shown in FIG. 8*a*, said protein having plasminogen-activating activity that is stimulated in the presence of a fibrin cofactor.

Another embodiment of the invention is a plasminogen-activating protein having a polypeptide sequence which is at least 90% homologous with the polypeptide sequence of amino acids 1–3 and 50–441 shown in FIG. 8*a*, said protein having plasminogen-activating activity that is stimulated in the presence of a fibrin cofactor.

Another embodiment of the invention is a plasminogen-activating protein having a polypeptide sequence which is at least 95% homologous with the polypeptide sequence of amino acids 1–3 and 87–441 (with the amino acid at position 88 changed from threonine to proline) shown in FIG. 8*a*, said protein having plasminogen-activating activity that is stimulated in the presence of a fibrin cofactor.

Another embodiment of the invention is a plasminogen-activating protein having a polypeptide sequence which is at least 90% homologous with the polypeptide sequence of amino acids 1–3 and 87–441 (with the amino acid at position 88 changed from threonine to proline) shown in FIG. 8*a*, said protein having plasminogen-activating activity that is stimulated in the presence of a fibrin cofactor.

The invention further relates to isolation and purification of the genetic information responsible for individual proteins and the methods of expressing the corresponding proteins.

Figure 1:
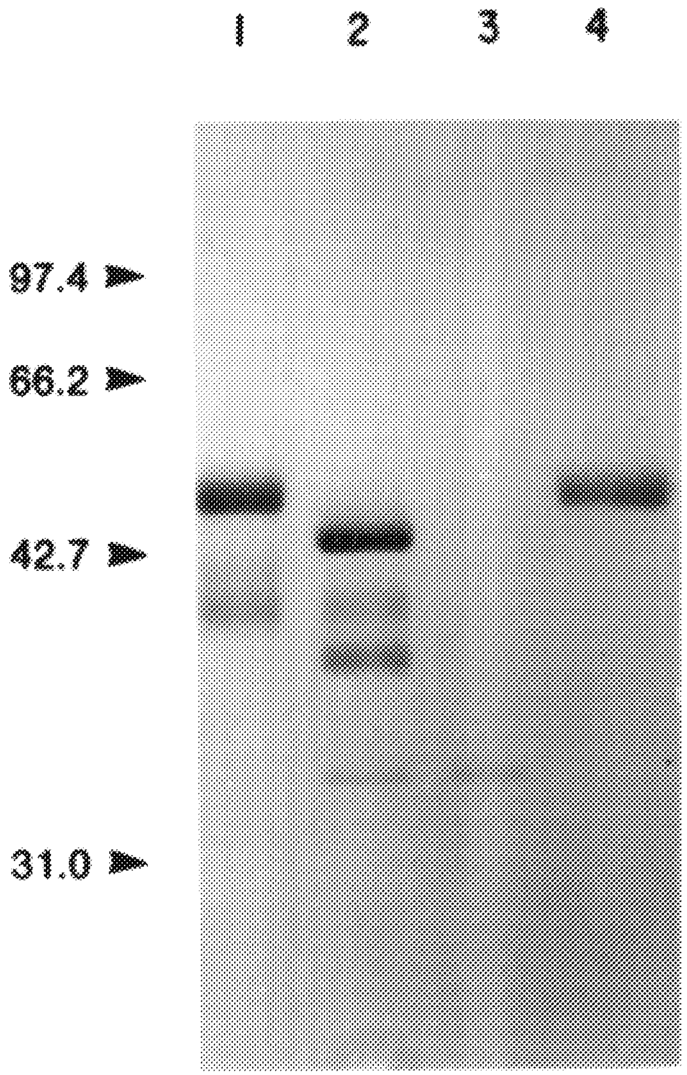
FIG. 1 shows SDS-polyacrylamide gel electrophoresis of purified vampire bat plasminogen activators. Samples were from vampire bat salivary glands (lanes 1 and 3) and saliva (lanes 2 and 4). Each sample was treated with endoglycosidase F prior to SDS-PAGE. Lanes 1 and 2: Western blotting and immunostain. Lanes 3 and 4: Fibrin autography.
Figure 2:
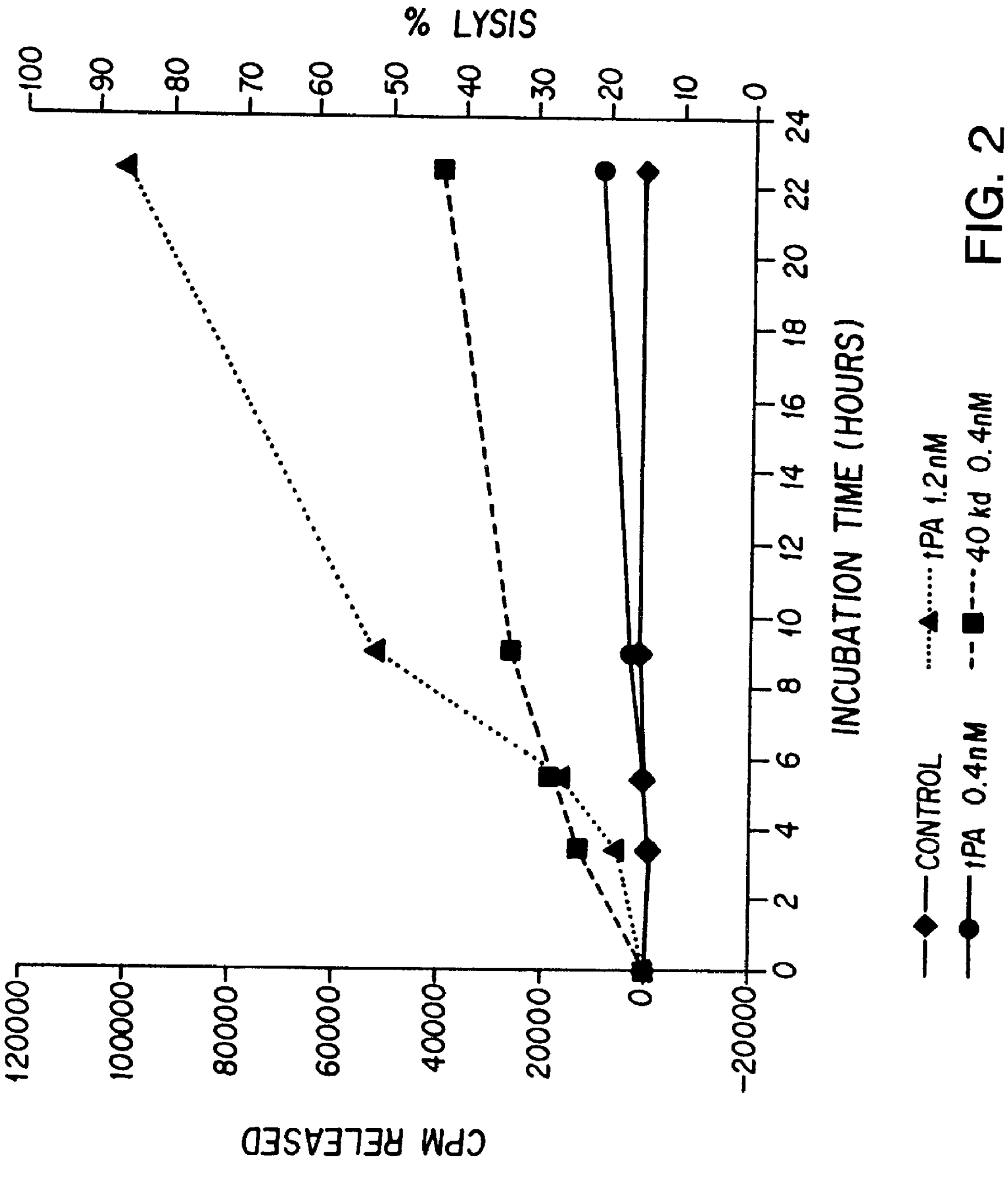
FIG. 2 shows % lysis of platelet poor plasma clots catalyzed by tPA and the 40 kd bat plasminogen activator protein.
Figure 3:
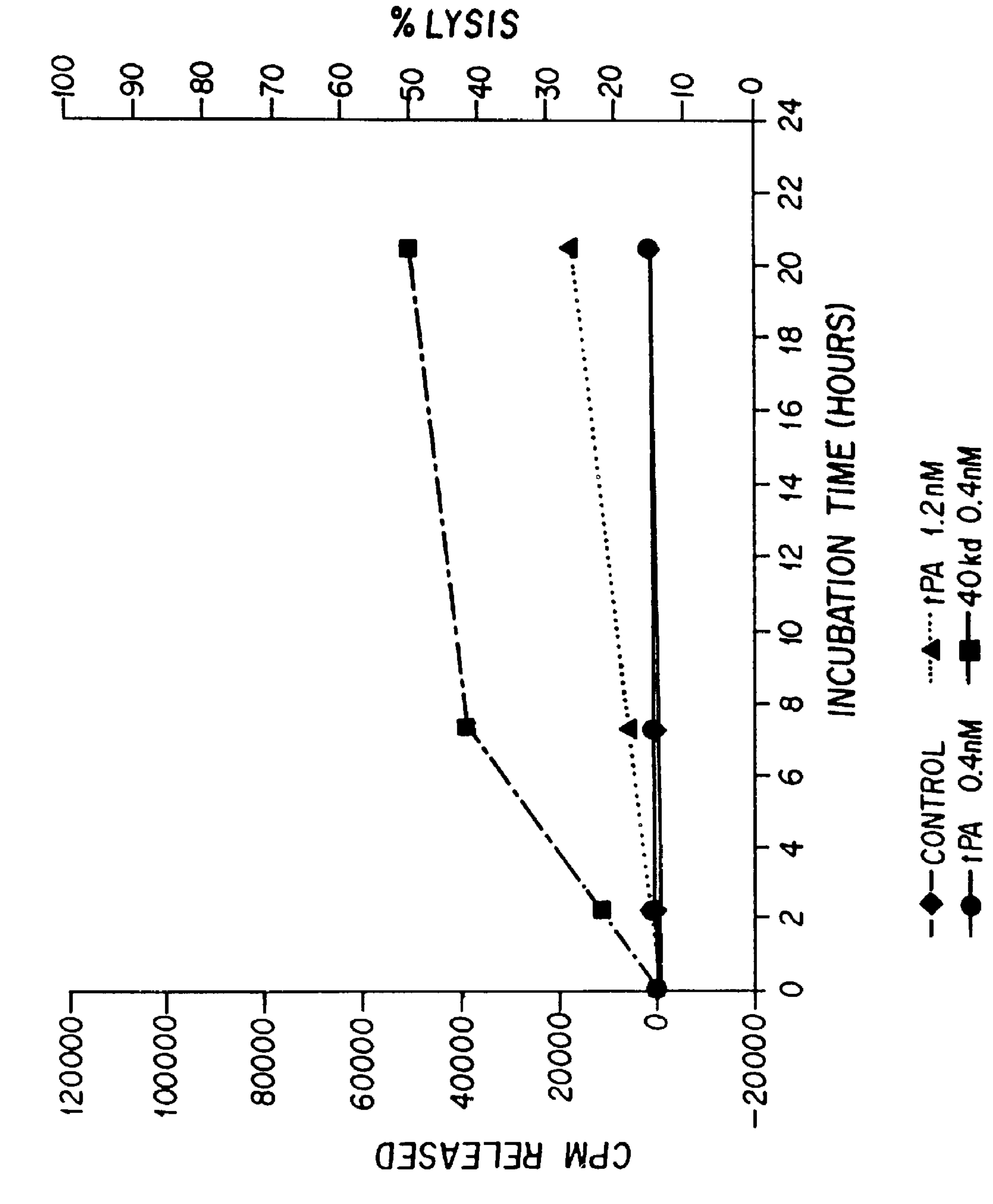
FIG. 3 shows % lysis of platelet rich plasma clots catalyzed by tPA and the 40 kd bat plasminogen activator protein.

FIG. 1, shows SDS-polyacrylamide gel electrophoresis (SDS-PAGE) of purified bat plasminogen activator. Samples were pretreated with 25 mM dithiothreitol prior to electrophoresis on a 11% stacking SDS-polyacrylamide gel. Lane 1, shows activator (3.6 ug) purified from vampire bat salivary glands; Lane 2, shows activator (3.6 ug) treated with endoglycosidase F (Boehringer Mannheim) (0.1 units for 24 hours at 37° C.); and Lane 3, 0.1 units of endoglycosidase F. Protein molecular weight markers are as indicated. Bat plasminogen activator (100 ng) from glands (Lane 1) and saliva (Lane 2) were analyzed by Western blotting using rabbit anti-bat plasminogen activator antibodies and alkaline-phosphatase conjugated, goat anti-rabbit IgG. Fibrin autography of activator (15 IU) from glands (Lane 3) and saliva (Lane 4) was carried out as described in Laemmli, U. K., *Nature,* 227, pp. 680–685 (1970).

To obtain the data presented in FIG. 1, frozen primary and accessory submandibular glands (6 g) from *Desmodus*

*rotundus* bats were placed in 40 ml of 10 mM Tris-HCl, 0.5M NaCl, pH 7.5, and immediately homogenized using a Brinkmann homogenizer. The homogenate was centrifuged at 27,000×g for 20 minutes. The supernatant fraction was clarified by centrifugation at 100,000×g for 30 minutes, diluted to 50 mM NaCl with 20 mM Tris-HCl, pH 7.0, 0.01% Tween 80 and applied to a phosphocellulose cation exchange column (Whatmann P11) equilibrated in 20 mM Tris-HCl, pH 7.2, 50 mM NaCl, and 0.01% Tween 80. Following sample application, the phosphocellulose column was washed exhaustively with the above equilibration buffer. Bat plasminogen activator was eluted from the phosphocellulose column with 20 mM Tris-HCl, pH 7.2, 0.5M NaCl and 0.01% Tween 80 and applied to an affinity column consisting of Erythrina trypsin inhibitor (ETI)(American Diagnostica) coupled to CNBr-activated Sepharose 4B (Pharmacia). The affinity column was washed with 20 mM $NaH_2PO_4$, 0.5M NaCl, pH 7.0, 0.1% Tween 80 and activator was subsequently eluted with 50 mM Na acetate, 0.2M NaCl, pH 4.0, 0.1% Tween 80. Fractions containing activator were pooled and a 1M Tris base was added to yield a final Tris concentration of 25 mM. The purified sample was stored at −70° C. Protein concentration was estimated with the Biorad dye-binding assay using bovine serum albumin as the standard.

Figure 6:
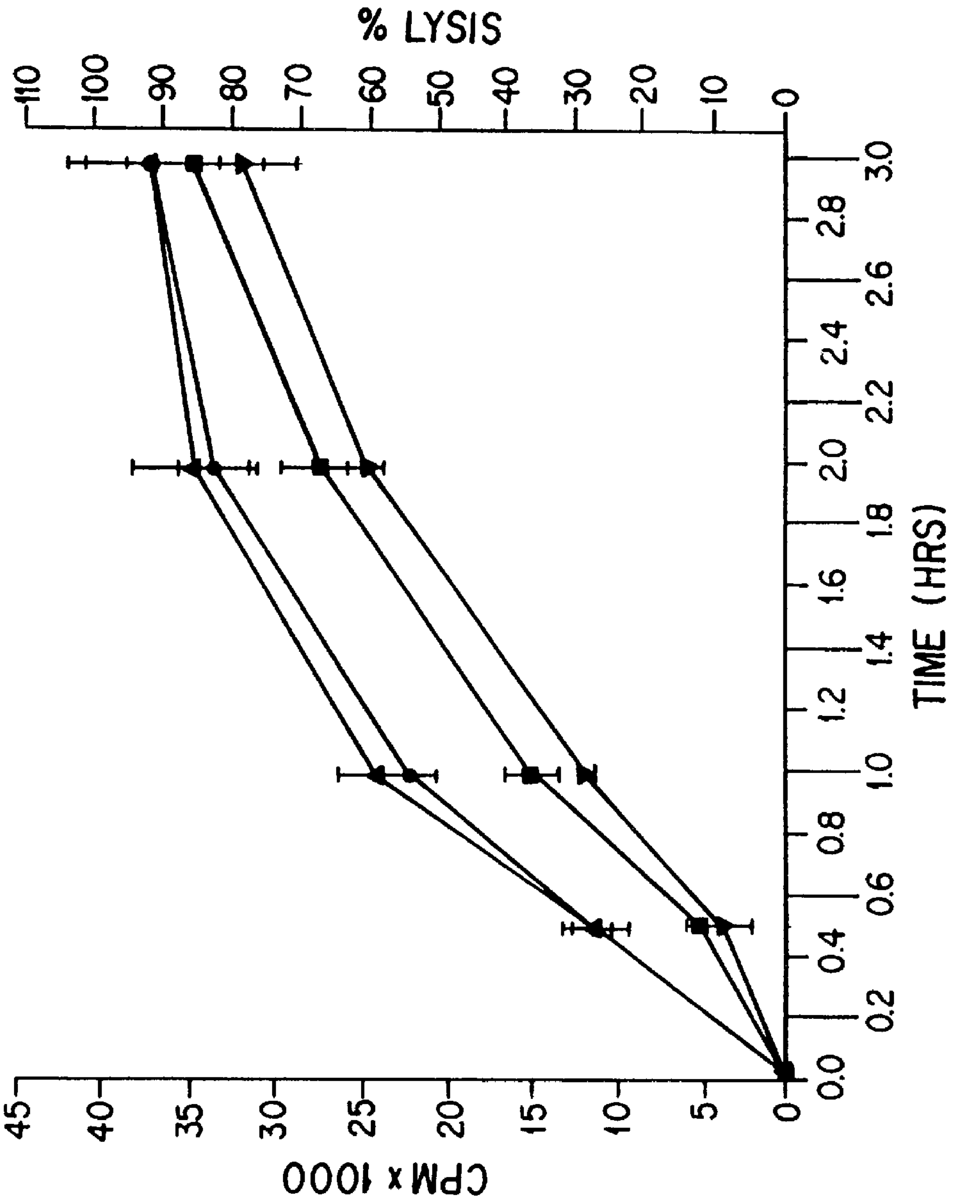
FIG. 6 shows clot lysis catalyzed by Bat-PA and tPA.

FIG. 6 shows clot lysis catalyzed by bat plasminogen activator and tPA. Plasma clots were formed by adding 0.2 IU of human thrombin (Sigma) and 7.5 mM $CaCl_2$ to 195 ul of human plasma containing [$^{125}I$] fibrinogen (100,000 cpm/clot). The final volume of each sample was 200 ul. The clots were formed in the presence of and adhered to small wooden sticks, aged for 30 minutes at 37° C., squeezed to express fluid and transferred to 250 ul of plasma to which was added 25 U/ml of Hirudin (Sigma). Twenty-five ul of 0.1M Tris-HCl, pH 8.0, 0.01% Tween 80 containing the plasminogen activator were added to the solution which bathed the clots, the samples were incubated at 37° C. and aliquots were removed and counted for soluble fibrin degradation products. Bat plasminogen activator purified from salivary glands and two-chain tPA were used for this study. ▼, 3nM Bat-PA; ■, 3nM t-PA; ●, 10 nM Bat-PA; ▲, 10 nM t-PA. Bat plasminogen activator and t-PA exhibited similar efficiences when monitored for their abilities to catalyze the release of radiolabelled fibrin degradation products from preformed plasma clots.

Figure 7:
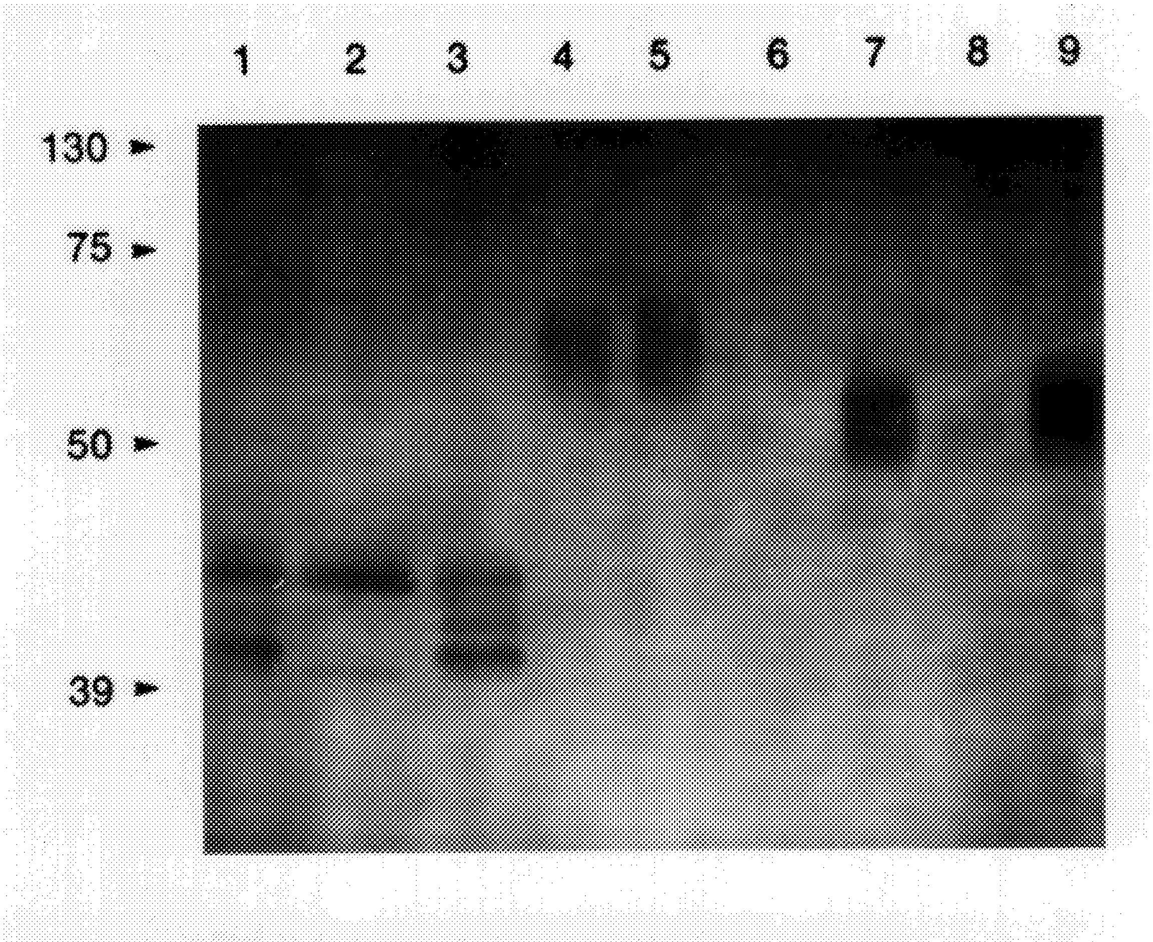
FIG. 7 shows binding of plasminogen activators to fibrin.

FIG. 7 shows binding of plasminogen activators to fibrin. Lane 1, Bat-PA, 1.8 pmoles; Lanes 2 and 3, 10% volume of the pellet and supernatant fractions, respectively, from the bat plasminogen activator containing fibrin sample; Lane 4, one-chain tPA, 1.8 pmole; Lanes 5 and 6, 10% volume of the pellet and supernatant fractions, respectively, from the tPA-containing fibrin sample; Lane 7, urokinase, 0.5 pmole; Lanes 8 and 9, 10% volume of the pellet and supernatant fractions, respectively, from the urokinase containing fibrin samples. The three bat plasminogen activator species (Lane 1) are unequally distributed between the supernatant and pellet fractions. The bulk of Bat-PA(H) partitions within the fibrin pellet (Lane 2) while Bat-PA(I) and Bat-PA(L) have no discernable affinity for fibrin and are predominently localized in the supernatant fraction (Lane 3). Aliquots of tPA (Lane 4) and urokinase (Lane 7) were also monitored for their ability to bind to fibrin. As expected, tPA binds tightly to fibrin and partitions within the pellet fraction (Lane 5) but urokinase is localized exclusively in the supernatant fraction (Lane 9).

Fibrin clots were formed by the addition of 0.2 IU of thrombin to 200 ul of 10 mM $NaH_2PO_4$, 140 mM NaCl, pH 7.4, 0.01% Tween 80 containing human fibrinogen (1 mg/ml), EDTA (5 mM) and bat plasminogen activator (18 pmole) or one-chain tPA (18 pmole) or urokinase (5.5 pmole). One-chain tPA was purified from a mixture of one-chain and two-chain tPA by chromatography with a monoclonal antibody column which preferentially binds one-chain tPA (PAM-1, American Diagnostica). Fibrin clots were aged for 1 hour at 37° C. and centrifuged at 100,000×g for 10 minutes. The pellet fractions were washed with 400 ul of $NaH_2PO_4$, NaCl, Tween 80 buffer, resuspended with 150 ul of 0.5% SDS and incubated at 37° C. for 1.5 hours with constant agitation. The pellet and supernatant fractions containing bat plasminogen activator were treated with Endo F. Samples were subjected to SDS-PAGE and analyzed by FA analysis.

Plasminogen Activator Assays

Fibrin Plate Method

Fibrin plates were formed by dissolving bovine or human fibrinogen (2 mg/ml) and human Glu-plasminogen (6 ug/ml) in 1% agarose solution (kept at 55° C.). Human thrombin (1.5 units) was then added prior to casting the mixed solution into calibrated immunodiffusion plates. Wells were punched out of a harden fibrin plate and column fractions were applied. Areas of lysis were observed where activity was present. The area of lysis ($mm^2$), per incubation time at 37° C., can be correlated to the units of activity of the enzyme.

Fibrin Autography

Samples are subjected to SDS-PAGE under non-reducing conditions and acrylamide gel is extensively washed in Triton X-100 (2.5%) and then placed on a plasminogen-containing fibrin agarose gel. The plasminogen activators renature due to the Triton treatment, and diffuse into the agarose gel where they activate plasminogen to yield plasmin. Generated plasmin degrades the fibrin resulting in the appearance of a zone of fibrinolysis which is readily recognized against the background of undegraded fibrin.

Coupled Amidolytic Assay

The activation of plasminogen to yield plasmin was examined in the presence of Desafib and production of plasmin was monitored with a colormetric plasmin substrate, Spectrozyme PL. The bat plasminogen activators were incubated with human Glu-plasminogen (20 ug/ml), Spectrozyme PL (0.4 mM), and Desafib (80 ug/ml). The mixture was incubated at 37° C. for 60 min. The reaction was terminated by addition of 50 ul of 10% SDS. Absorption of cleaved substrate was monitored at 405 nm. An activity unit of the bat plasminogen activators corresponds to that amount of enzyme which catalyzes the turnover of 1 $\mu$mole of Spectrozyme PL in 1 minute at 37° C.

Active Site Titration

Vampire bat plasminogen activators were titrated by two different techniques in order to determine functional molarity. The first technique was based on the principle of back-titration of a calibrated trypsin standard with a calibrated standard solution of a chloromethyl ketone inhibitor of both trypsin and plasminogen activators. A solution of trypsin (500 nM) was titrated directly using 4-methylumbellifery-p-guanidinebenzoate (MUGB). The chloromethyl ketone (Dansyl-glutamyl-glycyl-arginine chloromethyl ketone, DNS-EGRCK) was titrated against the MUGB-calibrated trypsin. Reaction of such a calibrated trypsin solution with a calibrated chloromethyl ketone solution allows measurement of the reduction in inhibition of the trypsin standard when the CK standard is preincubated with the activators. The presence of bat plasminogen activators results in an increase of activity relative to the trypsin-CK control which is proportional to the amount of plasminogen activator.

The second technique involved the observation of burst kinetics following the addition of MUGBE to the bat plasminogen activator when the reaction was carried out at low temperature (5° C.).

SDS-polyacrylamide Gel Electrophoresis

We used a modified protocol of the Laemmli system (*Nature,* 227, pp. 680–685 (1970)). Stacking and separating gels (0.75 mm) contained 4% and 10% polyacrylamide, respectively. The gels were run at 75 volts for 20 hours. Protein was detected by silver staining.

Purification of Bat Plasminogen Activator Proteins

Materials

The saliva and salivary glands of *Desmodus Rotundus* were purchased from Antibody Associates, Bedford, Tex. and from Dr. C. Rupprecht, Rabies Unit, Wistar Institute, Philadelphia, Pa. Fibrinogen, plasminogen, thrombin and substrates for amidolytic assay were from American Diagnostica, New York, N.Y. Materials used for electrophoresis were obtained from BioRad, Inc. and materials used for column chromatography were from Pharmacia. HPLC columns were the products of Vydac. Immunodiffusion plates were from ICN.

Procedure

Purification of the activators from vampire bat saliva involves phosphocellulose, phenyl-sepharose and C4 reverse phase HPLC chromatographic steps.

The saliva from vampire bat *Desmodus rotundus* was diluted to 3 times its volume with 10 mM Tris, pH 7.4, 50 mM NaCl, 0.01% Tween-20 solution. The diluted saliva was centrifuged for 5 min. at 12000 rpm, at 4° C., in an Eppendorf centrifuge. The supernatant was loaded directly onto a phosphocellulose column (25x10 cm) and washed with the same buffer used for dilution of the saliva. The column was run at a flow rate of 6 ml/hr. Activity was determined by the area of lysis using fibrin plate method and protein was monitored at O.D. 280.

Bat plasminogen activators bound tightly to phosphocellulose column. The recovery of activity following elution using 1M NaCl, was 94% (Table I).

Fractions from phosphocellulose column containing plasminogen activator activity were pooled and applied directly to a phenyl-sepharose column (1.5x5.0 cm) in the presence of 2.5M NaCl. The column was washed with a gradient of 2M NaCl to OM NaCl and 10% glycerol in 10 mM Tris buffer. Washing with 10% glycerol solution continued until all activity was eluted.

Figure 5:
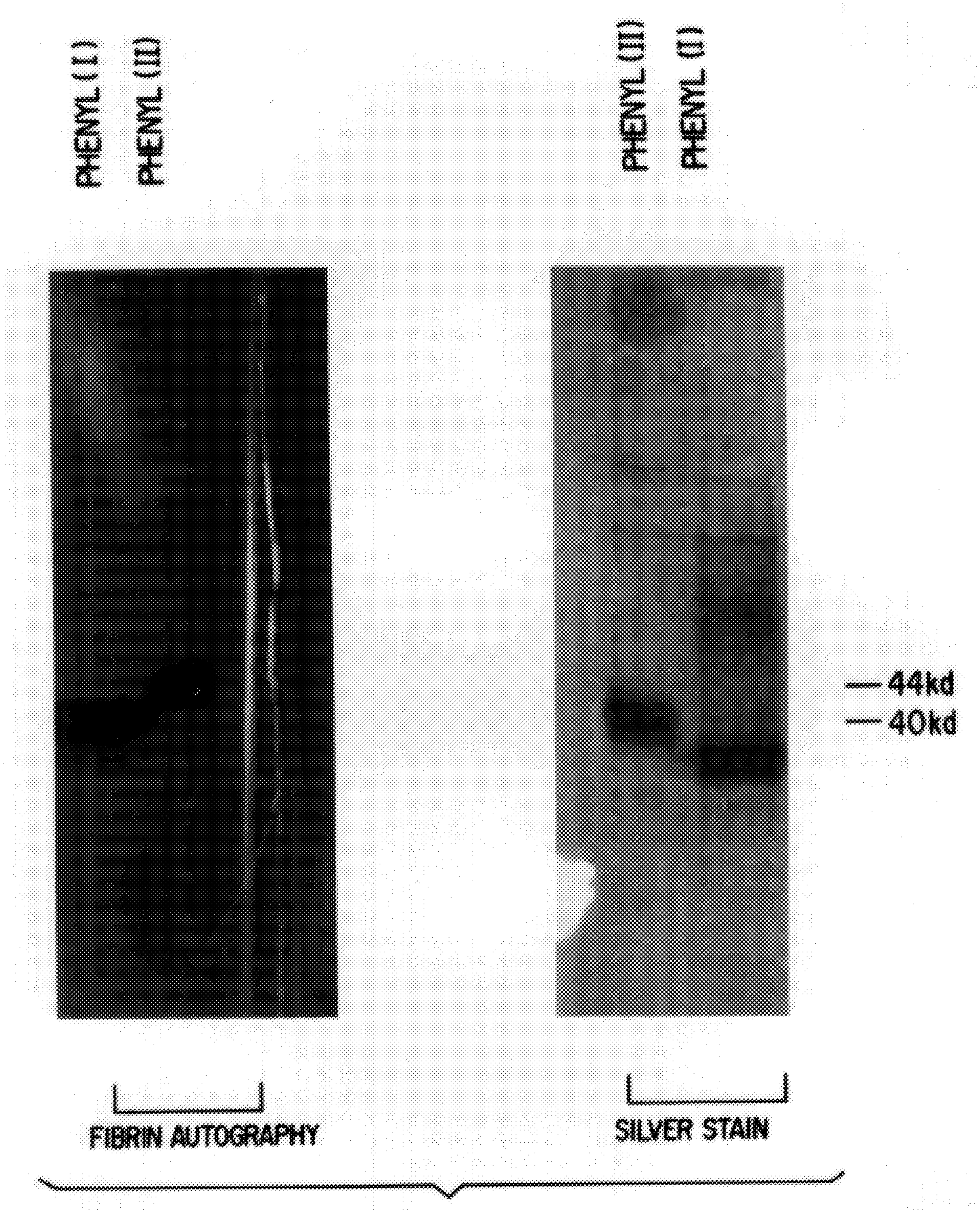
FIG. 5 shows molecular weight on SDS-PAGE of 40 kd and 45 kd proteins, identified by silver stain and Fibrin Autography.

Chromatography using the phenyl-sepharose column resulted in 82% recovery of activity (Table I). However, the activity was fractioned into two peaks, 1 and 2, which were pooled separately. The two peaks displayed different molecular weights as determined by silver stain following SDS-PAGE and Fibrin Autography (FIG. 5). Peak 1, which we believe represents Bat-PA(L), eluted towards the end of the salt gradient (2M-OM NaCl). We believe Peak 2 represents Bat-PA(I).

After phenyl-sepharose, we achieved about 660 fold of purification of Bat-PA(L). Total activity of the Bat-PA(I) enzyme was not determined optimally by amidolytic assay using plasminogen/spectrozyme PL coupling system, since Desafib is not an effective cofactor for this bat plasminogen activator.

TABLE I

Purification Table

| STEP | ACTIVITY | YIELD | PROTEIN |
|---|---|---|---|
| | UNIT | % | OD280 |
| BAT SALIVA (4 ML) | 206 | 100 | 76.230 |
| PHOSPHOCELLULOSE | 194 | 94 | 7.000 |
| PHENYL SEPHAROSE | | | |
| Peak 1 | 142 | 69 | 0.079 |
| Peak 2 | 27* | 13* | 0.083 |
| C4 REVERSE PHASE HPLC | | | |
| Peak 1 | 119 | 57 | N.D. |

*DESAFIB IS NOT AN APPROPRIATE COFACTOR FOR THIS SPECIES OF BAT PA. N.D. NOT DETERMINED.

The final purification step for the proteins was a C4 reverse phase HPLC column which had been equilibrated with 0.1% (v/v) trifluoroacetic acid (TFA) in water. Fraction-pools of the proteins were concentrated by lyophilization and applied directly to HPLC column. The enzyme was eluted by a gradient of 25% to 55% acetonitrile in the presence of 0.1% TFA. Protein peaks were monitored at O.D. 214 and collected separately. Volatile materials were removed by vacuum centrifugation, followed by lyophilization. The proteins were redissolved in 10 mM acetic acid. Activity was assayed using the fibrin plate method, after acetic acid was neutralized by Tris Tween buffer.

Purification of bat plasminogen activator from the vampire bat salivary glands was carried out as follows.

The primary and accessory submandibular glands from vampire bats are placed in buffer containing 10 mM Tris-HCl, 0.5M NaCl, 0.1% Tween 80, pH 7.5 and immediately homogenized using a polytron. Following centrifugation, the clarified SN fraction is both concentrated and equilibrated in 10 mM Tris-HCl, 50 mM NaCl, pH 7.2 through the use of an Amicon stirred cell (YM 10 membrane). The retentate is directly applied to a phosphocellulose column (Whatmann) equilibrated with 10 mM Tris-HCl, 50 mM NaCl, 0.01% Tween 80, pH 7.2. The plasminogen activator protein is quantitatively absorbed to the phosphocellulose column and step-eluted with 0.5M NaCl-supplemented application buffer. Activity recovery is typically greater than 80%.

Fractions containing activator activity were pooled and applied to an affinity column consisting of Erythrina trypsin inhibitor (ETI) coupled to Sepharose 4B. The bulk of the activity was absorbed to this column and effectively eluted by washing the column with 50 mM NaAcetate, pH 4.0, 0.2M NaCl and 0.1% Tween 80. The final recovery of bat plasminogen activator activity from the gland extract using this protocol was 91% yielding approximately 5.4 mg of bat plasminogen activator from 6 g of glands. The homogeneity of the bat plasminogen activator preparation was indicated by a correspondence of the estimated protein concentration and calculated functional molarity as determined by active-site titration using 4-methyl-umbelliferyl-p-guanidinobenzoate (Urano et al., *Biochem. Biophys Res. Comm.* 150, 45–51 (1988)).

Protein staining following SDS-PAGE of the pooled active fractions reveals a complex array of bands which exhibit a range of $M_r$ values. The migration of these species correspond to the zones of activity as defined by FA analysis. This correlation in addition to the agreement between amino acid analysis, N-terminal analysis and active site titration data provides evidence that the activator has been successfully purified to homogeneity.

Protein Characterization and Activity

Plasminogen activators of the present invention show no activity with plasminogen-free fibrin plates. Incubation of the activators with plasminogen in the presence of Fibrin I (Desafib) results in the generation of plasmin as judged by western blotting and immunostaining with an anti-plasmin (ogen) antibody. They exhibit activity towards human plasminogen bound to human fibrin as well as bovine plasminogen bound to bovine fibrin.

On sepharose G-200 gel filtration chromatography, bat plasminogen activator activity present in crude saliva was eluted as a broad peak with an approximate molecular weight of 130K. This molecular weight was probably an aggregated molecular weight of bat plasminogen activator. It appeared to be around 32K region on FPLC sepharose column in the presence of 0.01% Tween 20.

During purification studies, bat plasminogen activator failed to interact with lysine-sepharose, which was shown previously to be an effective step to purify proteins binding to fibrin via the kringle domain. Thus, the binding mechanism of the activators to fibrin is distinct from tPA.

Treatment of the activators with endoglycosidase H and F forms lower molecular weight active proteins, indicating that the activators are glycoproteins. The interaction of these proteins with wheat germ- and concanavalin A-agarose, provides further support for this conclusion.

The ability of Bat-PA(H) to activate Glu-plasminogen was evaluated with a coupled assay that monitored the turnover of a plasmin-specific amidolytic substrate (Table II). The specific activity (IU/nmol) of Bat-PA(H) towards Glu-plasminogen was approximately 260-fold less than tPA when assayed in the absence of a fibrin mimetic. However, the specific activity of Bat-PA(H) towards Glu-plasminogen in the presence of Desafib was approximately 85% of that exhibited by tPA. Hence, Desafib stimulated tPA and Bat-PA(H) activity by 205- and 45,000-fold, respectively. The specific activity exhibited by Bat-PA, the preparation containing the three molecular forms, was comparable to Bat-PA(H) in the absence of Desafib but approximately 30% less than Bat-PA(H) in the presence of this fibrin cofactor (Table II). We infer that the activities of Bat-PA(I) and Bat-PA(L) are not stimulated to the same extent as Bat-PA(H) by 80 ug/ml of Desafib.

TABLE II

Activation of Plasminogen by Bat-PA(H), Bat-PA and tPA

| Plasminogen | Desafib Concentration | | Fold |
|---|---|---|---|
| Activator | 0 ug/ml | 80 ug/ml | Stimulation |
| Bat-PA(H) | 1.05 ± 0.04 | 47,700 ± 4500 | 45,000 (220) |
| Bat-PA | 1.24 ± 0.08 | 33,500 ± 970 | 27,000 (130) |
| tPA | 270 ± 20 | 55,400 ± 1500 | 205 (1) |

These data report specific activities (IU/nmol) using the coupled amidolytic assay described above. Two-chain tPA was used for these assays; the catalytic activity of one-chain tPA is not reported since the results are confounded by the unavoidable generation of two-chain tPA during the assay. Desafib was included in the assay where indicated. The entries under the Fold Stimulation heading are the ratios of the specific activities in presence over the absence of Desafib. The numbers in parenthesis are stimulation of plasminogen activator activity by Desafib relative to that exhibited by tPA.

The abilities of tPA and Bat-PA(H) to catalyze lysis of plasminogen-containing fibrin clots were also compared. Slightly higher concentrations of Bat-PA(H) are required to achieve rates of clot lysis that are identical to those which result from concentrations of tPA ranging from 0.25 to 10 nM. The concentrations of tPA and Bat-PA(H) (derived from their dose-response curves) which give rise to selected clot lysis velocities are presented in Table III. The specific activity of Bat-PA(H) relative to tPA ranged from 59 to 72% and was correlated with plasminogen-activated concentration. The increased specific activity of Bat-PA(H) relative to tPA at higher concentrations may reflect differences between these plasminogen activators with respect to their modes of interaction with fibrin and/or plasminogen.

TABLE III

Fibrin Clot Lysis Mediated By tPA and Bat-PA(H)

| Velocity | tPA (nM) | Bat-PA(H) (nM) | Relative Efficacy % |
|---|---|---|---|
| 0.850 | 9.33 ± 1.11 | 12.9 ± 1.05 | 72.3 |
| 0.825 | 7.52 ± 0.88 | 10.53 ± 0.83 | 71.4 |
| 0.800 | 6.05 ± 0.69 | 8.60 ± 0.66 | 70.4 |
| 0.775 | 4.88 ± 0.54 | 7.02 ± 0.52 | 69.5 |
| 0.725 | 3.16 ± 0.34 | 4.68 ± 0.32 | 67.5 |
| 0.675 | 2.05 ± 0.21 | 3.12 ± 0.20 | 65.7 |
| 0.625 | 1.33 ± 0.13 | 2.08 ± 0.12 | 63.9 |
| 0.575 | 0.86 ± 0.08 | 1.39 ± 0.07 | 61.9 |
| 0.525 | 0.56 ± 0.05 | 0.92 ± 0.05 | 60.9 |
| 0.475 | 0.36 ± 0.03 | 0.61 ± 0.03 | 59.0 |
| 0.425 | 0.24 ± 0.02 | 0.41 ± 0.02 | 58.5 |

Clot-lysis experiments using the turbidimetric assay were carried out in quadruplicate with the following concentrations of 2-chain tPA or Bat-PA(H): 0.25, 0.50, 1.0, 2.5, 5.0, 7.5 and 10.0 nM. A clot lysis velocity was denoted as the maximal rate of decreasing turbidity (-mOD/min) as determined by analysis of each clot lysis profile with the Softmax kinetic software. Four and six independent linear dose-response curves (velocity vs. log [plasminogen activator]) were generated for tPA and Bat-PA(H), respectively. Listed in the table are the plasminogen-activator concentrations which result in the indicated clot lysis velocities. These values were derived from equations describing the best-fit lines constructed from analysis of all the dose-response curves for tPA and Bat-PA(H). The relative efficacy values are the ratios of the tPA over Bat-PA(H) concentrations which result in the indicated clot lysis velocity.

The bat plasminogen activators of the present invention are less susceptible than tPA to inactivation by the rapidly acting Type 1 plasminogen activator inhibitor (PAI-1).

It is believed that the concentration of PAI-1 in the area of an occluded vessel may be much greater than concentrations estimated from plasma studies. The existence of latent PAI-1 in plasma, and platelets containing PAI1 that can be released by thrombin, adenosine diphosphate and other platelet agonists, contributes to the relatively high local concentrations in occluded areas. PAI1 acts as an anti-activator that specifically blocks the activity of tPA.

Figure 4:
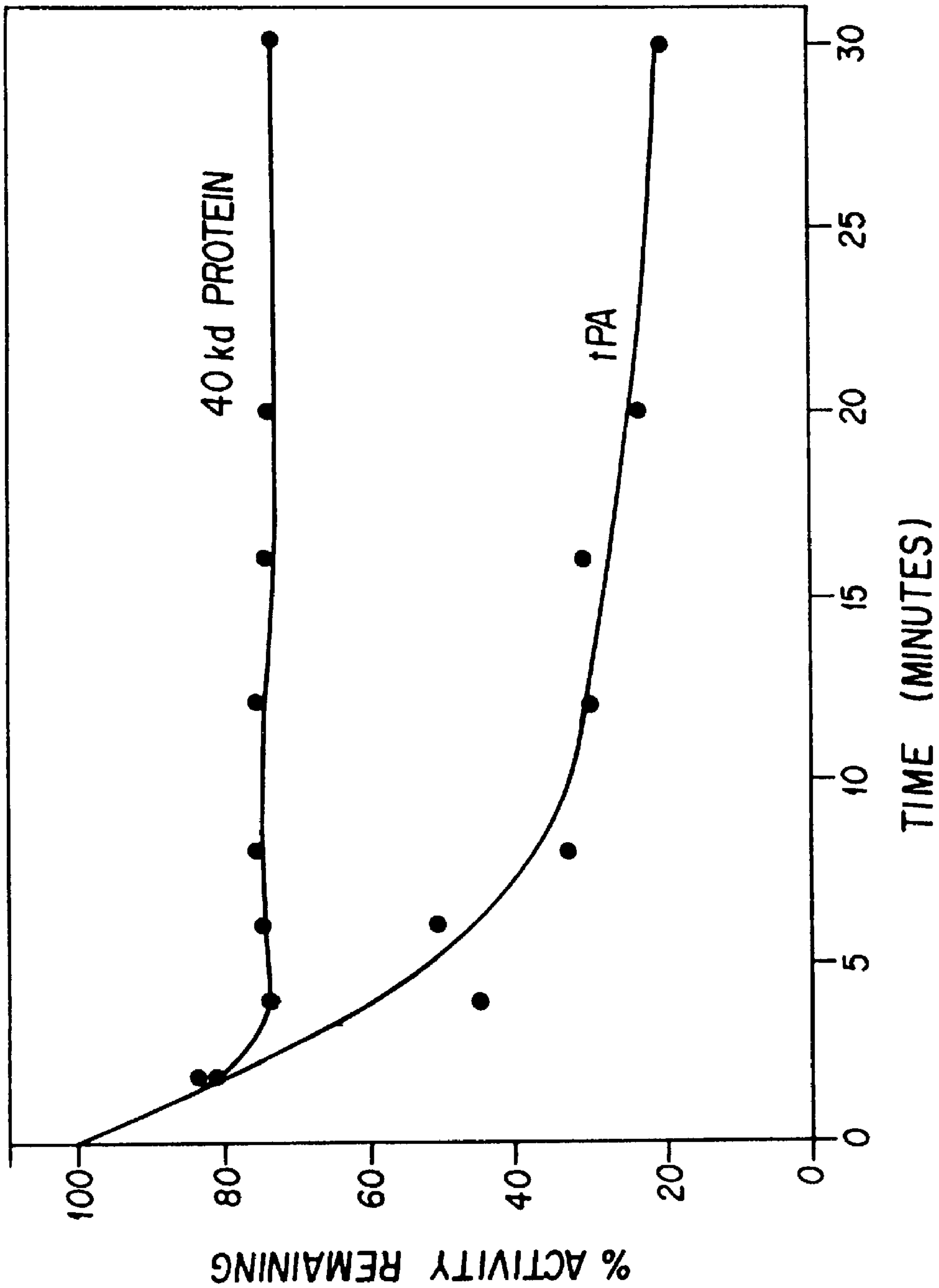
FIG. 4 shows inactivation of plasminogen activators by plasma components.

FIG. 4 shows that tPA is more readily inactivated by plasminogen activator inhibitors than are vampire bat saliva plasminogen activators. tPA and vampire bat saliva plasminogen activators were each incubated in plasma and their respective activities monitored as a function of time.

The NaCl-mediated inhibition of plasminogen activation by both tPA and the 40 kd protein was not observed when we monitored the lysis of fibrin clots. In this instance, clots were made from purified components which included fibrinogen (both labelled and unlabelled), plasminogen, $\alpha$ 2-antiplasmin, Factor XIIIa and buffer with or without 0.1M NaCl.

SDS-Polyacrylamide Gel Electrophoresis of Bat-PA and Blotting of Proteins onto Immobilon (PVDF Membranes)

Pooled active fractions from a trypsin inhibitor affinity column were obtained and further fractionated utilizing a Vydac C4 HPLC column, from which the plasminogen activator protein eluted at approximately 40% acetonitrile/ 0.1% trifluoroacetic acid. Two major peaks of activity (as determined by fibrin plate autolysis) could be detected which eluted from the HPLC column. The two peaks of activity were pooled separately and designated Bat-PA (I) and Bat-PA (II).

Using SDS-polyacrylamide gel electrophoresis (SDS-PAGE) followed by fibrin autography, both Bat-PA (I) and (II) display a similar pattern of lytic zones which ranged from molecular weights of 42,000–46,000 daltons. Both Bat-PA (I) and (II) could be labelled with $^3$H-DFP (diisopropylfluorophoshate), an active-site labelling reagent for serine proteinases.

Polyacrylamide gel electrophoresis of bat plasminogen activators designated I and II was performed using a modified protocol of the Laemmli system (*Nature,* 227, pp. 680–685 (1970)). Stacking and separating gels (0.75 mM) contain 4% and 10% polyacrylamide, respectively. The gels are run at 75 volts for 20 hours.

Proteins separated by SDS-polyacrylamide gel electrophoresis were electroblotted onto Immobilon (PVDF membranes) purchased from Millipore, Catalog No. IPVH304FO. The electroblotting of proteins was carried out essentially as described by Matsudaira (*J. Biol. Chem.* 262, pp. 10035–10038, 1987). Briefly, proteins are electroeluted from the SDS-polyacrylamide gel at 30 volts for a period of 15 hours. The Immobilon blot is then stained with Coomassie Blue to reveal bands of protein on the blot. The bands of protein are directly cut out from the blot and placed into the Model 477A Gas Phase Sequencer with a polybrene precondition filter beneath the blotted sample. The sequencer programs and reagents are those supplied by the manufacturer (Applied Biosystems). Released amino acid derivatives are identified by an on-line HPLC system.

N-terminal Amino Acid Sequences of Plasminogen Activators from Vampire Bat Saliva N-terminal sequencing of SDS-PAGE fractionated plasminogen activator was carried out using a polyvinylidene difluoride membrane (Immobilon, Millipore) and an Applied Biosystems model 470 sequenator with on-line PTH analysis (Matsudaira, P., *J. Biol. Chem.* 262, 10035–10038 (1987) ). V8-fragments of plasminogen activator were generated by reduction/alkylation of the activator with dithiothreitol/ iodoacetamide, incubation of the modified protein with *Staphylococcus aureus* V8 protease (Boehringer Mannheim), and isolation of proteolytic fragments using a Vydac C-18 HPLC column. The active site peptide fragment, T1, was identified as follows: plasminogen activator was incubated with [1,3-$^3$H] diisopropyl fluorophosphate (New England Nuclear) in the presence of Desafib (American Diagnostica), treated with dithiothreitol and iodoacetamide, digested with trypsin, and the radiolabeled fragment was isolated by HPLC and submitted for sequence analysis.

Eight protein bands displaying plasminogen activator activity were identified on the Immobilon blot and subjected to sequence analysis. The sequences obtained are listed below: A -( )-indicates no amino acid could be identified at that particular position, most likely due to the instability and poor recovery of certain amino acids from the protein sequencer.

Band 1—Ala-Tyr-Gly-Gly-Pro-Ser-Glu-( )-Arg-Tyr-Phe

Band 2—Ala-Tyr-Gly-Gly-Pro-Ser-Ala-( )-( )-Tyr-( )-Asp-Gln-Gly-Val

Band 3—Ala-Tyr-Gly-Val-Ala-Cys-Lys-Asp-Glu-Ile-Thr-Gln-Met-(Thr)-Tyr

Band 4—Ala-Tyr-Gly-Val-Ala-Cys-Glu-Asp-Glu-Ile-Thr-Gln-Met-(Thr)-Tyr-Lys

Band 5—Ala-Tyr-Gly-Gly-Pro-Ser-Glu-Leu-( )-Tyr-Phe-Ile-Gly-Gly

Band 6—Ala-Tyr-Gly-Asp-Pro-His-Ala-Thr-Ala-Tyr-Lys-Asp-Gln-Gly-Val

Band 7—Ala-Tyr-Gly-Asp-Pro-His-Ala-Thr-Cys-Tyr-Lys-Asp-Gln-Gly-Val-Thr-Tyr-Arg-Gly Band 8—Ala-Tyr-Gly-Asp-Pro-His-Ala-Thr-Cys-Tyr-Lys-Asp-Gln-Gly-Val-Thr-Tyr-Arg-Gly-Thr

Molecular Cloning of the Bat Plasminogen Activator cDNA

Recombinant DNA technology is defined herein as technology which allows segments of genetic information, DNA, from different cells, usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated and incorporated into an appropriate cloning vector, and transfected into an appropriate host cell.

Cloning vector as used herein is defined as a DNA sequence which allows the incorporation of specific experimental foreign DNA, with the combined DNA being introduced into a host cell that can exist in a stable manner and express the protein dictated by the experimental DNA. The foreign DNA combined with the vector DNA constitutes a recombinant DNA molecule which is derived from recombinant technology. Cloning vectors may include plasmids, bacteriophage, viruses and cosmids. It is to be understood that any cloning vector may be used to clone the novel Desmodus protein DNA sequences. Expression vectors are defined herein as DNA sequences that are required for the transcription of cloned copies of genes and the translation of their mRNAs in an appropriate host. Such vectors can be used to express either procaryotic or eucaryotic genes in a variety of cells such as bacteria, yeast, insect and mammalian cells. The proteins may also be expressed in a number of virus systems. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The proteins of the present invention may exist as, but are not limited to, the complete proteins specified by the defined genes in Desmodus native protein or as any fragment or subunit thereof, or as hybrids of the complete protein or its fragments or subunits, provided the proteins exhibit properties of a plasminogen activator derived from *Desmodus rotundus* saliva having a stringent requirement for the presence of fibrin. The complete proteins, as used herein, refers to the full length post-transcriptionally modified polypeptide produced by the appropriate Desmodus genes. The complete proteins may be obtained by purification from *Desmodus rotundus* saliva or by expression in an appropriate expression vector of the corresponding recombinant derived gene product. Protein fragments or subunits refers to any portion of the protein which contains fewer amino acids than the complete protein and retains the ability to activate plasminogen under the same conditions as does the native protein. Hybrid proteins include, but are not limited to, fusion proteins or proteins resulting from the expression of multiple genes within the expression vector. A fusion protein is defined as one in which a limited number of amino acids coded for by the expression vector are expressed and the expression results in their attachment to the specific plasminogen activator polypeptide. Proteins resulting from multiple genes may include the specific activator polypeptide linked to a second polypeptide or peptides by peptide bonds that enhance plasminogen activation.

Salivary glands were obtained from 10 freshly killed vampire bats and used for the isolation of poly A+RNA. This RNA was used to construct a λ gt 22 unidirectional cDNA library consisting of more than $2\times10^6$ recombinant bacteriophage. An additional RNA preparation used for Northern blotting analysis was isolated from glands which were quick frozen on dry ice. The quality of this RNA was comparable to that isolated from fresh tissue.

Total RNA was isolated from the primary and accessory submandibular glands of vampire bats (*Desmodus rotundus* ) by the low temperature guanidinium thiocyanate method (Han, J. et al, *Biochem.* 26, 1617–1625 (1987). Poly(A)+ RNA was isolated by oligo(dT)-cellulose chromatography. Double stranded cDNA was prepared by a modification of the method of Gubler and Hoffman (*Gene* 25, 263–269 (1983)) as previously described (Dixon, R. A. F. et al. *Nature* 321, 75–79 (1986)). The cDNA was size fractionated by agarose gel electrophoresis into pools of 1–2 kb and 2–7 kb lengths which were ligated to the EcoRI site of lambda ZAP arms (Stratagene). The libraries were amplified on *E. coli* strain LE392 and screened by plaque hybridization as described (Maniatis, T., et al., Molecular Cloning: A Laboratory Manuel, Cold Spring Harbor Laboratory, Cold Spring Harbor, N.Y.). Pairs of partially overlapping complementary oligonucleotides corresponding to peptides N-1, N-3, V-2 and T-1 were annealed, labelled with Klenow fragment and four [32P]alpha-dNTPs, and used to probe nitrocellulose filter lifts from the libraries. Hybridization and washing conditions were as described (Maniatis et al., ibid). Positive clones were plaque purified and the cDNA inserts rescued by coinfection with a helper phage as per the suppliers instructions. Single and double stranded DNA sequencing was performed by the dideoxynucleotide method. Sanger, F. et al. *Proc. Natl Acad. Sci, U.S.A.,* Vol. 74, pp. 5463–5467 (1977).

FIG. 8*a* shows nucleotide sequence of the plasminogen activator(s) cDNA and amino acid sequence of the activator (s). The nucleotide sequence extends from the 5' end of the longest clone and through the open reading frame. An additional 800 nt of 3' untranslated sequence, ending in a poly(A) tail are not shown. The nucleotide sequence is numbered at the left of each line with the proposed initiation codon being the first base. The predicted amino acid sequence is shown in single letter code and numbered at the right of each line. The amino acid sequences determined for Bat-PA(H), Bat-PA(I) and Bat-PA(L) are underlined and designated as N-1, N-2 and N-3, respectively. Bat-PA(H) corresponds to a full-length form in which the signal peptide is cleaved at a position analogous to the signal cleavage site in tPA. Bat-PA(I) begins with the same three amino acids as Bat-PA(H) followed by sequences beginning with N-2 corresponding to the EGF domain. Hence, Bat-PA(I) corresponds to a finger-minus form of Bat-PA(H). Bat-PA(L)'s unique amino-acid sequence begins with the same three amino acids, followed by that portion of the polypeptide beginning at N-3, except the second amino acid of N-3 is changed from threonine to proline, after the EGF domain and gives rise to a finger-minus and EGF-minus form of the protein. The amino acid sequences of two staphlycoccus V8 proteolytic fragments (V-1, V-2), and a tryptic fragment (T-1) are also underlined. Dashed underlining indicates amino acid residues which could not be determined or which disagreed with the amino acids predicted from the cDNA. The location of the active site Ser which was labelled with $[^3H]$ DIFP is indicated (*). The predicted N-linked glycosylation sites are indicated by the boxed amino acids.

Oligonucleotide primers were synthesized based upon three phage clones containing BatPA cDNA. The BatPA cDNA clones were subjected to polymerase chain reaction (PCR)-effected amplification (see U.S. Pat. No. 4,800,159, col. 2, lines 36–68, col. 3–4 and col. 5, lines 1–20, hereby incorporated by reference). The cDNA strands were heated until they separated, at which time the primers that bind to each strand were added. The primers instructed DNA polymerase, which performs its replication function, to copy a particular portion of the strand. The process was continued with a series of heating and cooling cycles, heating to separate strands, and cooling as the copies were made. The cycles were repeated to generate more and more copies of the special strands. Through amplification, the coding domain to which terminal restriction sites are appended was obtained.

Expression vectors for the three bat plasminogen activator forms (Bat-PA(H), Bat-PA(I) and Bat-PA(L)) were prepared, as described below, and then transfected into cells according to a transient transfection protocol (used to qualitatively determine whether successful expression is achieved) or a stable transfection protocol (preferably used to establish viable clones).

In the transient transfection protocol, $2.5\times10^6$ cells/100 mm dish are plated in 10 ml media 24 hours prior to transfection. Two to four hours prior to transfection, the media is changed. A DNA/CaPO4 precipitate is prepared by preparing filter sterilized recombinant BatPA-pD5 plasmid DNA in a concentration of 5 $\mu$g/250 $\mu$l dd$H_2O$ for each 100 mm dish. This is mixed with 500 $\mu$l of 0.5M $CaCl_2$ and dd$H_2O$ to final volume of 1 ml. One ml of 2×HBS is added dropwise with light agitation. The preparation is left standing at room temperature for 10–30 minutes, and the precipitate is dropped to the plate evenly with gentle swirling. After this step, the protocol differs slightly depending on the cells to be transfected. CV1 cells are incubated four hours at 37° C. and 10% $CO_2$, while COS7 and 293 cells are incubated four hours at 37° C. and 6% $CO_2$. Four hours post transfection, media is removed for 293 cells. Four hours post transfection, CV1 and COS7 cells are subjected to glycerol shock for 2 minutes (15% glycerol in media) and rinsed 2×with PBS. Fresh media is then added. Cells are incubated at 37° C. and asayed 24, 48 and 72 hours post transfection.

In the stable transfection protocol, the transient transfection protocol is followed with the following modifications. $5\times10^5$ cells per 100 mm dish are plated out rather than $2.5\times10^6$ per 100 mm dish. 0.5 $\mu$g of Neo expression plasmid is included in the DNA/$CaPO_4$ precipitate for G418 selection. Cells are kept in selection for 48 hours with media change at 2–3 day intervals until G418 resistant colonies develop.

Intermediate and expression vectors were prepared in the following manner for the various bat plasminogen activator forms.

I. Bat-PA(H)

1. 5' Natural NTL

Bat-PA(H) cDNAs were derived from the cDNA library by PCR amplification of cDNA using oligodeoxy-nucleotide pairs 141 & 142 and 27 & 19 shown below as primers:

```
                  Bgl II
141  5'>ATA TAT AGA TCT AGG GAC ACC GCA CAA
     ATG GTG>3'

                  Spe I    Bgl II
142  5'>ATA TAT GAG CTC AGA TCT CAG GGA GTT
     GCG TAT TCT TGG>3'

              Hind III           Spe I
 27  5'>ATA TAA GCT T AC TAG TAG GGA CAC CGC
     ACA AAT GGT G>3'
         met

                  XbaI        Sac I
 19  5 >TAT ATC TAG A GA GCT CCA GGG AGT TGC
     GTG TTC TTG G>3'
```

Figure 9:
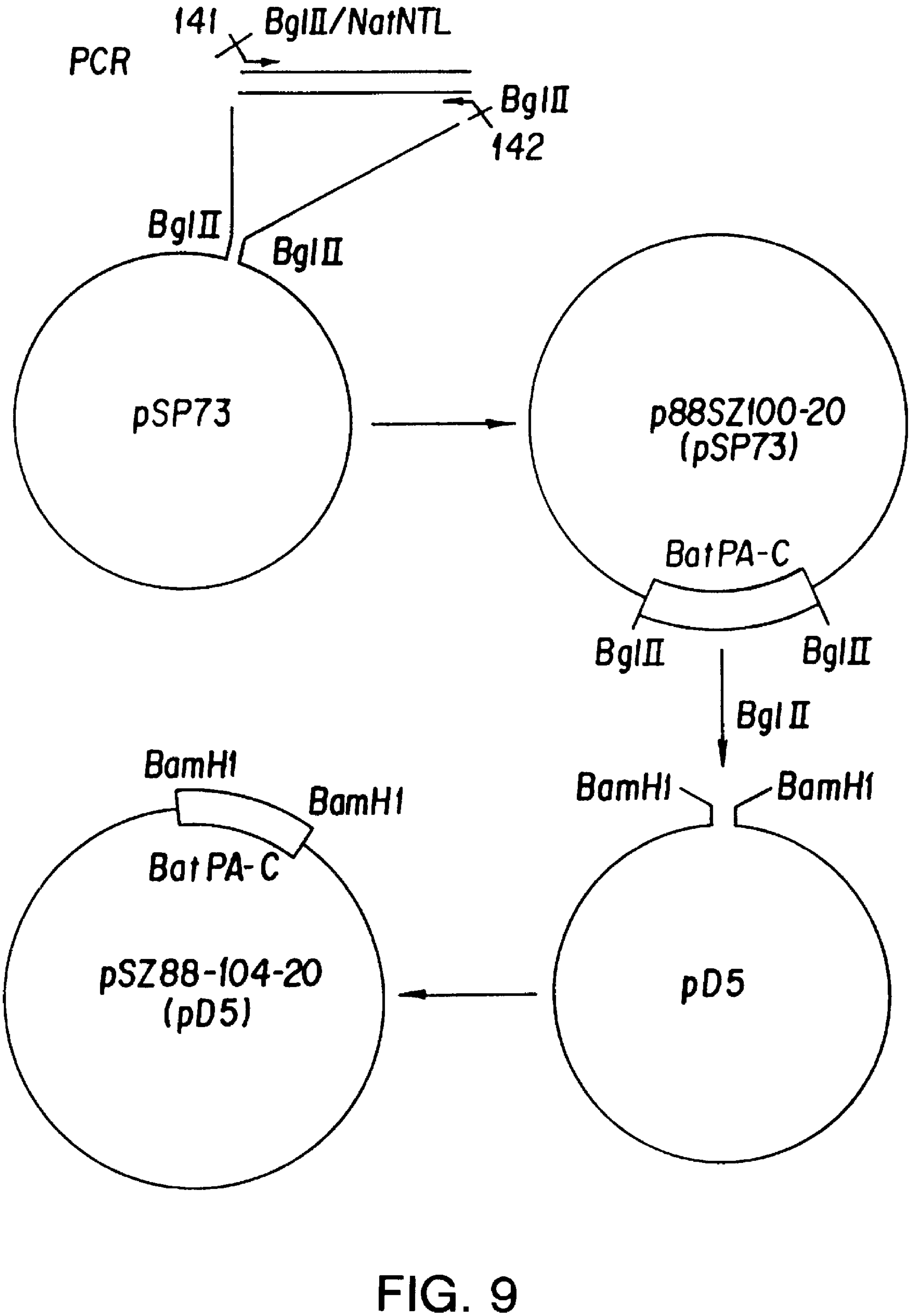
FIG. 9 depicts is schematic form the synthesis of plasmid p88SZ-100-20 which is derived from known plasmid pSP73 and which contains the Bat-PA(H) gene sequence, and ultimately the synthesis of plasmid pSZ88-104-20 which is derived from known plasmid pD5 and which contains the Bat-PA(H) gene sequence.

PCR was carried out in a 100 $\mu$l reaction volume composed of 10 mM Tris-Cl pH 8.3, 50 mM KCl, 1.5 mM $MgCl_2$, 200 $\mu$M in each dNTP, 100 pmole of each PCR primer, 10–100 ng of cDNA or library DNA and 2.5 units of Taq polymerase. The reaction was programmed in a DNA thermocycler for 30 cycles. Each cycle included two minutes denaturation at 94° C., two minutes annealing at 60° C. and two minutes polymerization at 72° C. Amplified cDNAs were gel purified and then restricted by BglII and ligated into the pSP73 BglII site. Following sequence verification, the Bat-PA(H) open reading frames were subcloned into the eukaryotic expression vector pD5 containing the adenovirus major late promoter to generate pSZ88-104-20 (see FIG. 9). 293 cells were transfected with pSZ88-104-20 to generate 293-Bat-PA-1 mammalian cells (ATCC No. CRL 10180). *E. coli* cells were transfected with pSZ88-104-20 to generate BPA-CN-pSZ88-104-20 bacterial cells (ATCC No. 68050).

2. 5' Kozak NTL

Bat-PA(H) cDNAs were PCR amplified as described above using oligodeoxynucleotide pairs 18 & 19 as primers:

```
           Hind III    Spe I          Nco I
18  5'>ATA TAA GCT TAC TAG TCC ACC ATG GTG
                                       met
    AAT ACA ATG AAG AC>3'
```

Figure 10:
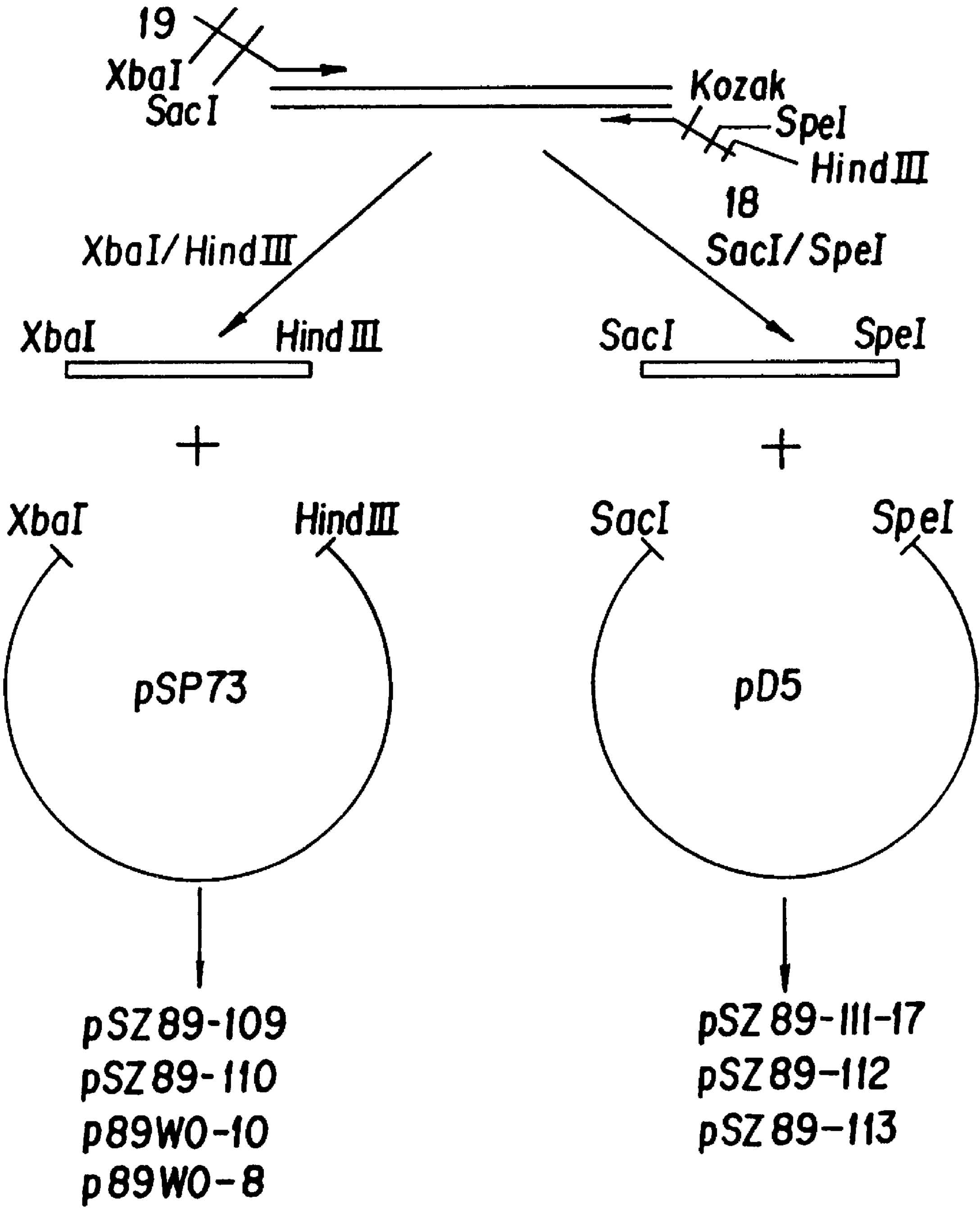
FIG. 10 depicts in schematic form the synthesis of plasmids pSZ89-109, pSZ89-110, p89WO-10 and p89WO-8 which are derived from known plasmid pSP73 and which contain the Bat-PA(H) gene sequence, and plasmids pSZ89-111, pSZ89-112 and pSZ89-113 which are derived from known plasmid pD5 and which contain the Bat-PA(H) gene sequence.

Amplified cDNAs were gel purified and then cleaved by XbaI and Hind III followed by ligation into the intermediate vector pSP73 between its XbaI and Hind III sites to generate pSZ89-109, pSZ89-110, p89WO-10 and p89WO-8. The Bat-PA(H) open reading frames were additionally subcloned into the Sac I/Spe I site of pD5-mcs vector which contains a multi-cloning site in place of the original BamHI cloning site to generate pSZ89-111-17, pSZ89-112 and pSZ89-113 (see FIG. 10). *E. coli* cells were transfected with pSZ89-111-17 to generate BPA-CK-pSZ89-111-17 bacterial cells (ATCC No. 68052).

II. Bat-PA(I)

Figure 11:
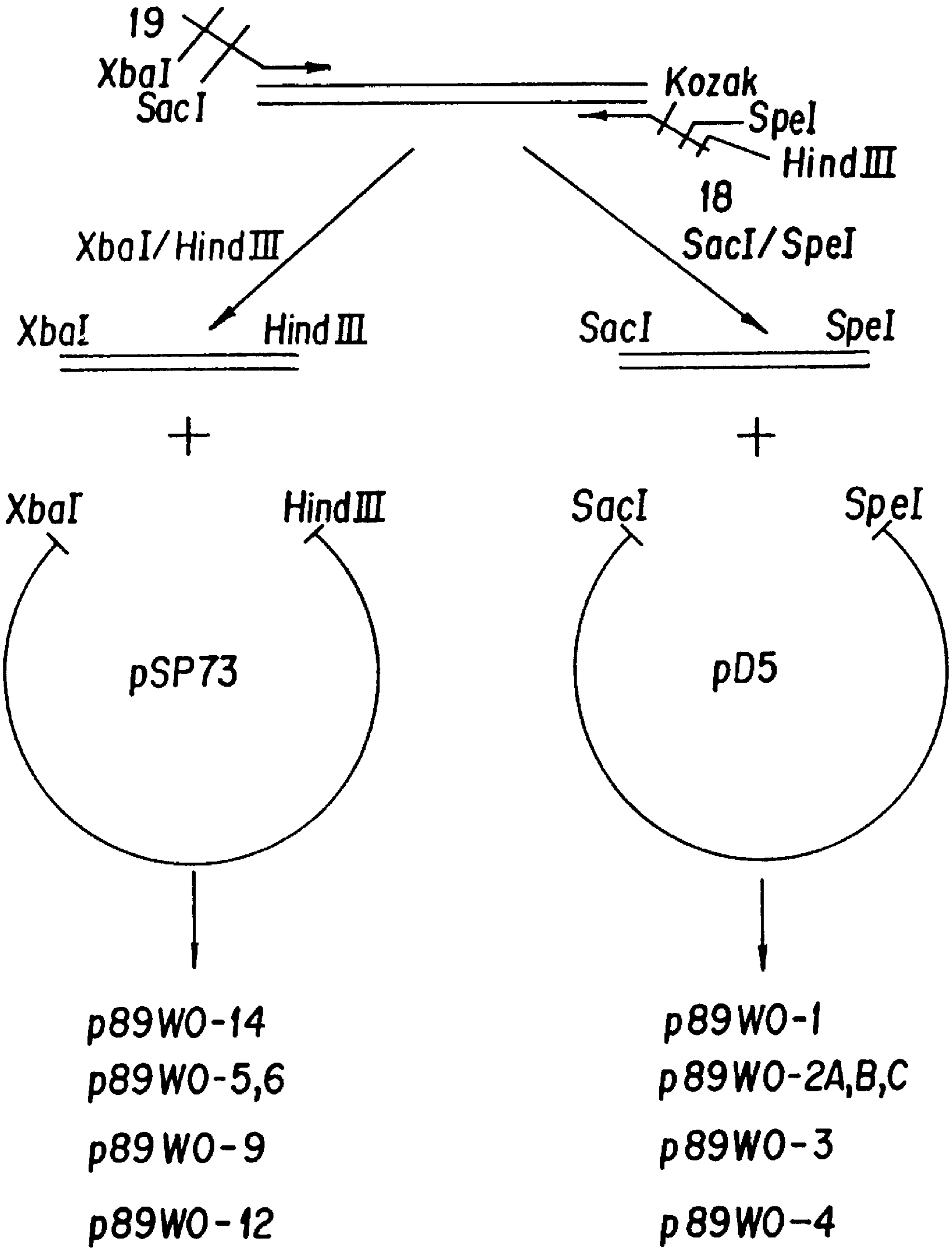
FIG. 11 depicts in schematic form the synthesis of plasmids p89WO-14, p89WO-5,6, p89WO-9 and p89WO-12 which are derived from known plasmid pSP73 and which contain the Bat-PA(I) gene sequence, and plasmids p89WO-1, p89WO-2A,B,C, p89WO-3 and p89WO-4 which are derived from known plasmid pD5 and which contain the Bat-PA(I) gene sequence.

Bat-PA(I) open reading frames were derived from the cDNA library by the same PCR procedure described above and recognized by their smaller size relative to the complete isoform. Bat-PA(I) containing the natural NTL were derived from oligodeoxynucleotide pair 27 & 19 whereas the Bat-PA(I) containing the Kozak NTL were derived from oligodeoxynucleotide pair 18 & 19. Amplified Bat-PA(I) open reading frames were cleaved by Hind III and XbaI for cloning into pSP73 to generate p89WO-14, p89WO-5,6, p89WO-9 and p89FWO-12 or cleaved by Spe I and Sac I for cloning into the pD5-mcs vector to generate p89WO-1, p89WO-2,A,B,C, p89WO-3 and p89WO-4 (see FIG. 11). *E. coli* cells were transfected with p89WO-1 to generate BPA-FK-p89WO-1 bacterial cells (ATCC No. 68051). *E. coli* cells were transfected with p89-WO-2C to generate BPA-FN-p89WO-2C bacterial cells (ATCC No. 68053).

III. Bat-PA(L)

Bat-PA(L) open reading frames were derived from the cDNA library by the same PCR amplification of library DNA with oligodeoxynucleotide pair 18 & 11.4 as primers.

11.4 5>CCT TTC TCC TGA TGA CCT TC>3'

Amplified DNA was gel purified and then cut with NcoI and the smallest of the three NcoI fragments, which encodes the 5' portion of Bat-PA(L), was again gel purified and ligated to NcoI cleaved p89WO-11 (a Bat-PA(H) open reading frame in pSP73) to get p89WP-17 and p89WP-18, respectively. The Bat-PA(L) open reading frames were then released from the intermediate vectors by cleavage with Sac I and Spe I and subcloned into pD5-mcs vector giving rise to p89W-20A&B and p89WP-19A&B (see FIG. 12). *E. coli* cells were transfected with p89WP-20A to generate BPA-DK-p89WP-20A bacterial cells (ATCC No. 68049).

Fibrin agar plate assays of conditioned media removed at 48 hours post-transfection of COS-7 revealed 50 ng/mL of BatPA.

Clone pSZ88-104-20 was found to be the best expresser. This clone was established in 293 cells and expressed more than 0.5 micrograms per milliliter per day of BatPA activity/confluent monalayer. Chronic exposure to butyrate and medium optimization boosted the level of expression to more than 10 micrograms per milliliter per day. Other suitable expression vectors are pSZ89-111-17 (a derivative of pSZ88-104-20 with a Kozak rather than a natural 5'-NTL), EBV/EBNA/D5BatPA-C and CMVIE-AKl-BatPA-C, and HIV LTR/BatPA-C.

Comparison to human tissue plasminogen activator

Presented below is a comparison of the primary amino acid sequence structure of human tissue plasminogen activator and Bat-PA(H) of the invention.

| | | | | | | | | | | | | |
|---|---|---|---|---|---|---|---|---|---|---|---|---|
| | 1 | | | | | | | | | 10 | | |
| human t-Pa | G | A | R | S | Y | Q | V | I | C | R | D | E |
| Bat-PA(H) | G | S | R | A | Y | G | V | A | C | R | D | E |
| | −3 | | | | | | | | | 7 | | |
| | | | | | | | | 20 | | | | |
| | K | T | Q | M | I | Y | Q | Q | H | Q | S | W |
| | K | T | Q | M | I | Y | Q | Q | Q | E | S | W |
| | | | | | | | | 17 | | | | |
| | | | | | | 30 | | | | | | |
| | L | R | P | V | L | R | S | N | R | V | E | Y |
| | L | R | P | E | V | R | S | K | R | V | E | H |
| | | | | | | 27 | | | | | | |
| | | | | 40 | | | | | | | | |
| | C | W | C | N | S | G | R | A | Q | C | H | S |
| | C | R | C | D | R | G | L | A | Q | C | H | T |
| | | | | 37 | | | | | | | | |
| | | 50 | | | | | | | | | | 60 |
| | V | P | V | K | S | C | S | E | P | R | C | F |
| | V | P | V | K | S | C | S | E | L | R | C | F |
| | | 47 | | | | | | | | | | 57 |
| | | | | | | | | | | 70 | | |
| | N | G | G | T | C | Q | N | A | L | Y | F | S |
| | N | G | G | T | R | W | N | A | A | S | F | S |
| | | | | | | | | | | 67 | | |

-continued

80
D F V C N C P E G F A G
D F V C N C P K G Y T G
77

90
K C C E I D T R A T C Y
K Q C E V D T H A T C Y
87

100
human t-PA E D Q G I S Y R G T W S
Bat-PA(H) K D Q G V T Y R G T W S
97

110 120
T A E S G A E C T N W N
T S E S G A Q C I N W N
107 117

130
S S A L A N K P Y S G R
S N L L T R R T Y N G R
127

140
R P D A I R L G L G N H
R S D A I T L G L G N H
137

150
N Y C R N P D R D S K P
N Y C R N P D N N S K P
147

160
W C Y V F K A G K Y S S
W C Y V I K A S K F I L
157

170 180
E F C S T P A C S E G N
E F C S V P V C S K A
167 176

190
human t-PA S D C Y F G N G S A Y R 200
human t-PA G T H S L T E S G A S C

210
L P W N S M I L I G K V

220
Y T A Q N P S A Q A L G 230 240
L G K H N Y C R N P D G

250
D A K P W C H V L K N R

260
R L T W E Y C D V P S C 270
human t-PA S T C G L R Q Y S Q P Q
Bat-PA(H) T C G L R K Y K E P Q
177 180

280
F R I K G G L F A D I A
L H S T G G L F T D I T
190

290 300
human t-PA S H P W Q A A I F A K H
Bat-PA(H) S H P W Q A A I F A Q N
200 210

-continued

310
R R S P G E R F L C G G
R R S S G E R F L C G G
220

320
I L I S S C W I L S A A
I L I S S C W V L T A A
230

330
H C F Q E R F P P H H L
H C F Q E R Y P P Q H L
240

340
T V I L G R T Y R V V P
R V V L G R T Y R V K P
250

350 360
G E E E Q K F E V E K Y
G K E E Q T F E V E K C
260 270

370
I V H K E F D D D T Y D
I V H E E F D D D T Y N
280

380
N D I A L L Q L K S D S
N D I A L L Q L K S G S
290

390
human t-PA S R C A Q E S S V V R T
Bat-PA(H) P Q C A Q E S D S V R A
300

400
V C L P P A D L Q L P D
I C L P E A N L Q L P D
310

410 420
W T E C E L S G Y G K H
W T E C E L S G Y G K H
320 330

430
E A L S P F Y S E R L K
K S S S P F Y S E Q L K
340

440
E A H V R L Y P S S R C
E G H V R L Y P S S R C
350

450
T S Q H L L N R T V T D
T S K F L F N K T V T K
360

460
N M L C A G D T R S G G
N M L C A G D T R S G E
370

470 480
P Q A N L H D A C Q G D
I H P N V H D A C Q G D
380 390

490
human t-PA S G G P L V C L N D G R
Bat-PA(H) S G G P L V C M N D N H
400

-continued

| | | | | | | | | | | | |
|---|---|---|---|---|---|---|---|---|---|---|---|
| | | | | | 500 | | | | | | |
| M | T | L | V | G | I | I | S | W | G | L | G |
| M | T | L | L | G | I | I | S | W | G | V | G |
| | | | | | 410 | | | | | | |
| | | | | 510 | | | | | | | |
| C | G | Q | K | D | V | P | G | V | Y | T | K |
| C | G | E | K | D | I | P | G | V | Y | T | K |
| | | | | 420 | | | | | | | |
| | | 520 | | | | | | | | | |
| V | T | N | Y | L | D | W | I | R | D | N | M |
| V | T | N | Y | L | G | W | I | R | D | N | M |
| | | 430 | | | | | | | | | |
| 530 | | | | | | | | | | | |
| R | P | | | | | | | | | | |
| R | P | | | | | | | | | | |
| 440 | | | | | | | | | | | |

The fibronectin finger domain of human tPA (sequence 9–46) has 78% homology with Bat-PA(H) sequence 6–43. The epidermal growth factor domain of human tPA (sequence 46–95) has 75% homology with the Bat-PA(H) sequence 43–92. The first kringle domain of human tPA (sequence 95–177) has 67% homology with Bat-PA(H) sequence 92–174.

The second kringle domain of human tPA (sequence 178–265) has no counterpart in Bat-PA(H). Bat-PA(H) amino acids 175 and 176 are lysine and alanine. Amino acids 190–441 of Bat-PA(H), the "light chain", have 74% homology with human tPA light chain sequence 280–531.

Figure 8B:
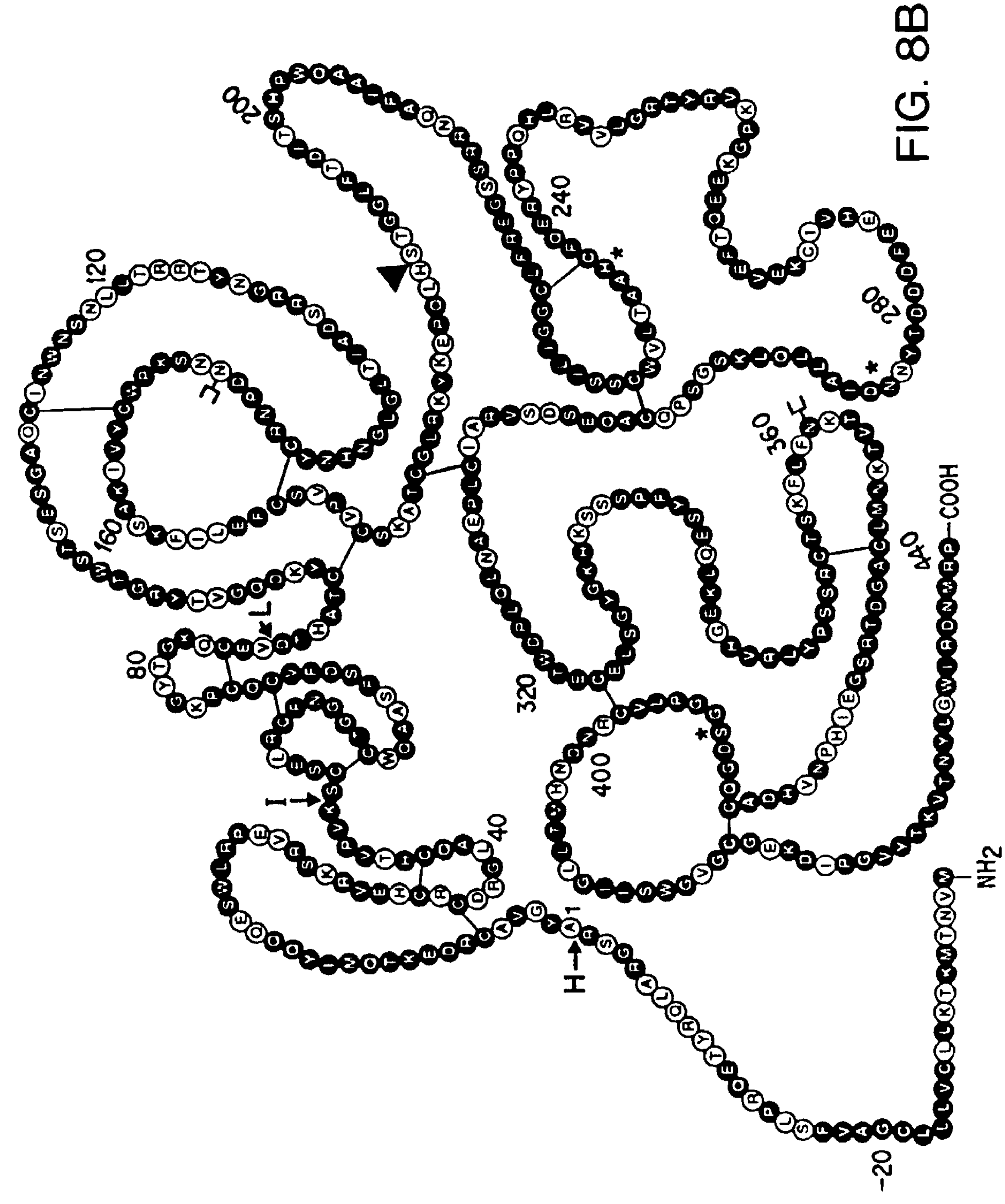
FIG. 8B shows a schemetic representation of the amino-acid sequence of vampire bat plasminogen activator and comparison with human tPA.

FIG. 8*b* is a schematic representation of the amino-acid sequence of Bat-PA(H) and comparison with human t-PA (Pennica et al. *Nature* Vol. 301, 214–221 (1983)). The individual amino acids of Bat-PA are indicated as single letter code. The closed circles show amino acid identity between Bat-PA(H) and human t-PA. Open circles represent divergent residues. The proposed disulfide pattern is by analogy to t-PA. The postulated N-linked glycosylation sites are indicated by an attached bracket.

In addition to the natural derivatives Bat-PA(I) and Bat-PA(L) of this plasminogen activator, other derivatives within the present invention are plasminogen activators excluding either the finger domain region (amino acids (−3)–43) or the epidermal growth factor region (amino acids 43–84). Another derivative is Bat-PA(H) having mutated carbohydrate holding amino acid residues. Each exhibits desirable plasminogen activating characteristics, including longer half-life.

Also within the scope of the invention are fusion proteins of the light chain Bat-PAs (sequence 190–441) and the heavy chain human tPA (sequence 1–278), and derivatives thereof having plasminogen activating properties. Since the proteolytic domains of Bat-PAs are not significantly inactivated by type-1 plasminogen activator inhibitor, we believe that the fusion proteins would have improved pharmacological properties over human tissue plasminogen activator.

As previously mentioned, activity of bat plasminogen activators is dramatically stimulated in the presence of a fibrin cofactor. It appears to be at least 90-fold more selective then tPA towards fibrin-bound plasminogen. The second kringle domain of tPA harbors a lysine-binding site which is believed to play a decisive role in mediating fibrin-induced stimulation of activity. In contrast, the amino-acid sequence of the activator of the present invention reveals that its marked fibrin-selectivity is not due to the presence of a region similar to the second kringle domain of tPA. Furthermore, the inability of bat plasminogen activators to bind to Lys-sepharose shows that the presence of a lysine-binding site is not responsible for the fibrin-specific activation of plasminogen.

The kringle domain of the activators of the invention mediates fibrin-induced stimulation of activity despite its differences with the second kringle region of tPA.

The activators also differ structurally from tPA by the absence of a plasmin-sensitive processing site in the bat enzyme.

The Bat-PA proteins described above has been defined by means of determined DNA gene and deductive amino acid sequencing. It will be understood that natural allelic variations exist. These variations may be demonstrated by (an) amino acid difference(s) in the overall sequence or by deletions, substitutions, insertions, inversions or additions of (an) amino acid(s) in said sequence. In addition, the location of and degree of glycosylation will depend on the nature of the host cellular environment.

The potential exists, in the use of recombinant DNA technology, for the preparation of various bat plasminogen activator derivatives, variously modified by resultant single or multiple amino acid substitutions, deletions, additions or replacements, for example, by means of site directed mutagenesis of the underlying DNA. All such allelic variations and modifications resulting in derivatives of bat plasminogen activator are included within the scope of this invention so long as the essential, characteristic bat plasminogen activator activity remains unaffected in kind. The bat plasminogen activator is prepared (1) having methionine as its first amino acid (present by virtue of the ATG start signal codon insertion in front of the structural gene) or (2) where the methionine is intra- or extracellularly cleaved, having its normally first amino acid, or (3) together with either its signal polypeptide or a conjugated protein other than the conventional signal polypeptide, the signal polypeptide or conjugate being specifically cleavable in an intra- or extracellular environment (see British Patent Application Publication No. 2,007,676A), or (4) by direct expression in mature form without the necessity of cleaving away any extraneous, superfluous polypeptide. The latter is particularly important where a given host may not, or not efficiently, remove a signal peptide where the expression vehicle is designed to express the plasminogen activator together with its signal peptide. In any event, the thus produced bat plasminogen activator, in its various forms, is recovered and purified to a level fitting it for use in the treatment of various vascular conditions or diseases.

Therapeutic Treatment

These proteins may be administered by any convenient means which will result in its delivery into the blood stream in substantial amount. Intravenous administration is presently contemplated as the preferred administration route. They are soluble in water, and may therefore be effectively administered in solution.

In one exemplary application, a suitable amount of proteins of the present invention is intravenously administered to a heart attack victim. Suitable doses for achieving thrombolysis are up to 200 mg, preferably between 25 mg and 150 mg, and more preferably between about 25 mg and 50 mg.

The proteins may also be applied at the above-mentioned doses by successive bolus injections over a period of several hours.

The proteins may be co-administered with platelet aggregation inhibitors to produce the combined effect of thrombolysis and platelet aggregation inhibition. Co-administration includes intravenous administration of the platelet aggregation inhibitors in an amount to inhibit platelet aggregation, e.g. an amount which achieves a steady state plasma concentration of between 0.05–2 $\mu$M.

What is claimed is:

1. A purified plasminogen activator, wherein said activator i. is activated by a fibrin cofactor;

ii. catalyzes lysis of plasma clots;

iii. is isolatable from saliva or salivary glands of a bat of the genus Desmodus; and iv. has an apparent molecular weight of about 40,000–46,000 daltons, as determined by SDS polyacrylamide gel electrophoresis analysis under nonreducing conditions.

2. A plasminogen activator of claim 1, further wherein said activator v. is substantially less inactivated by plasma inhibitor PAI-1 than human tPA;

vi. has an apparent molecular weight of about 38,000–44,000 daltons, as determined by SDS polyacrylamide gel electrophoresis analysis under reducing conditions, after deglycosylation with endoglycosidase F;

vii. has an activity stimulation of at least 27,000-fold in the presence of fibrin co-factor;

viii. does not have a domain corresponding to the kringle 2 domain, amino acids 178–265, of human tPA; and ix. does not have a plasmin-sensitive processing site.

3. A purified plasminogen activator of claim 2, having the amino acid sequence

Ala-Tyr-Gly-Asp-Pro-His-Ala-Thr-Cys-Tyr-Lys-Asp-
Gln-Gly-Val-Thr-Tyr-Arg-Gly-Thr-Trp-Ser-Thr-Ser-
Glu-Ser-Gly-Ala-Gln-Cys-Ile-Asn-Trp-Asn-Ser-Asn-
Leu-Leu-Thr-Arg-Arg-Thr-Tyr-Asn-Gly-Arg-Arg-Ser-
Asp-Ala-Ile-Thr-Leu-Gly-Leu-Gly-Asn-His-Asn-Tyr-
Cys-Arg-Asn-Pro-Asp-Asn-Asn-Ser-Lys-Pro-Trp-Cys-
Tyr-Val-Ile-Lys-Ala-Ser-Lys-Phe-Ile-Leu-Glu-Phe-
Cys-Ser-Val-Pro-Val-Cys-Ser-Lys-Ala-Thr-Cys-Gly-
Leu-Arg-Lys-Tyr-Lys-Glu-Pro-Gln-Leu-His-Ser-Thr-
Gly-Gly-Leu-Phe-Thr-Asp-Ile-Thr-Ser-His-Pro-Trp-
Gln-Ala-Ala-Ile-Phe-Ala-Gln-Asn-Arg-Arg-Ser-Ser-
Gly-Glu-Arg-Phe-Leu-Cys-Gly-Gly-Ile-Leu-Ile-Ser-
Ser-Cys-Trp-Val-Leu-Thr-Ala-Ala-His-Cys-Phe-Gln-
Glu-Arg-Tyr-Pro-Pro-Gln-His-Leu-Arg-Val-Val-Leu-
Gly-Arg-Thr-Tyr-Arg-Val-Lys-Pro-Gly-Lys-Glu-Glu-
Gln-Thr-Phe-Glu-Val-Glu-Lys-Cys-Ile-Val-His-Glu-
Glu-Phe-Asp-Asp-Asp-Thr-Tyr-Asn-Asn-Asp-Ile-Ala-
Leu-Leu-Gln-Leu-Lys-Ser-Gly-Ser-Pro-Gln-Cys-Ala-
Gln-Glu-Ser-Asp-Ser-Val-Arg-Ala-Ile-Cys-Leu-Pro-
Glu-Ala-Asn-Leu-Gln-Leu-Pro-Asp-Trp-Thr-Glu-Cys-
Glu-Leu-Ser-Gly-Tyr-Gly-Lys-His-Lys-Ser-Ser-Ser-
Pro-Phe-Tyr-Ser-Glu-Gln-Leu-Lys-Glu-Gly-His-Val-
Arg-Leu-Tyr-Pro-Ser-Ser-Arg-Cys-Thr-Ser-Lys-Phe-
Leu-Phe-Asn-Lys-Thr-Val-Thr-Lys-Asn-Met-Leu-Cys-
Ala-Gly-Asp-Thr-Arg-Ser-Gly-Glu-Ile-His-Pro-Asn-
Val-His-Asp-Ala-Cys-Gln-Gly-Asp-Ser-Gly-Gly-Pro-
Leu-Val-Cys-Met-Asn-Asp-Asn-His-Met-Thr-Leu-Leu-
Gly-Ile-Ile-Ser-Trp-Gly-Val-Gly-Cys-Gly-Glu-Lys-
Asp-Ile-Pro-Gly-Val-Tyr-Thr-Lys-Val-Thr-Asn-Tyr-
Leu-Gly-Trp-Ile-Arg-Asp-Asn-Met-Arg-Pro or a glycosylated form, microheterogeneous form or allelic variant thereof.

4. A purified plasminogen activator of claim 2, having the amino acid sequence

Ala-Tyr-Gly-Val-Ala-Cys-Arg-Asp-Glu-Lys-Thr-Gln-
Met-Ile-Tyr-Gln-Gln-Gln-Glu-Ser-Trp-Leu-Arg-Pro-
Glu-Val-Arg-Ser-Lys-Arg-Val-Glu-His-Cys-Arg-Cys-
Asp-Arg-Gly-Leu-Ala-Gln-Cys-His-Thr-Val-Pro-Val-
Lys-Ser-Cys-Ser-Glu-Leu-Arg-Cys-Phe-Asn-Gly-Gly-
Thr-Cys-Trp-Gln-Ala-Ala-Ser-Phe-Ser-Asp-Phe-Val-
Cys-Gln-Cys-Pro-Lys-Gly-Tyr-Thr-Gly-Lys-Gln-Cys-
Glu-Val-Asp-Thr-His-Ala-Thr-Cys-Tyr-Lys-Asp-Gln-
Gly-Val-Thr-Tyr-Arg-Gly-Thr-Trp-Ser-Thr-Ser-Glu-
Ser-Gly-Ala-Gln-Cys-Ile-Asn-Trp-Asn-Ser-Asn-Leu-

-continued

Leu-Thr-Arg-Arg-Thr-Tyr-Asn-Gly-Arg-Arg-Ser-Asp-
Ala-Ile-Thr-Leu-Gly-Leu-Gly-Asn-His-Asn-Tyr-Cys-
Arg-Asn-Pro-Asp-Asn-Asn-Ser-Lys-Pro-Trp-Cys-Tyr-
Val-Ile-Lys-Ala-Ser-Lys-Phe-Ile-Leu-Glu-Phe-Cys-
Ser-Val-Pro-Val-Cys-Ser-Lys-Ala-Thr-Cys-Gly-Leu-
Arg-Lys-Tyr-Lys-Glu-Pro-Gln-Leu-His-Ser-Thr-Gly-
Gly-Leu-Phe-Thr-Asp-Ile-Thr-Ser-His-Pro-Trp-Gln-
Ala-Ala-Ile-Phe-Ala-Gln-Asn-Arg-Arg-Ser-Ser-Gly-
Glu-Arg-Phe-Leu-Cys-Gly-Gly-Ile-Leu-Ile-Ser-Ser-
Cys-Trp-Val-Leu-Thr-Ala-Ala-His-Cys-Phe-Gln-Glu-
Arg-Tyr-Pro-Pro-Gln-His-Leu-Arg-Val-Val-Leu-Gly-
Arg-Thr-Tyr-Arg-Val-Lys-Pro-Gly-Lys-Glu-Glu-Gln-
Thr-Phe-Glu-Val-Glu-Lys-Cys-Ile-Val-His-Glu-Glu-
Thr-Phe-Glu-Val-Glu-Lys-Cys-Ile-Val-His-Glu-Glu-
Phe-Asp-Asp-Asp-Thr-Tyr-Asn-Asn-Asp-Ile-Ala-Leu-
Leu-Gln-Leu-Lys-Ser-Gly-Ser-Pro-Gln-Cys-Ala-Gln-
Glu-Ser-Asp-Ser-Val-Arg-Ala-Ile-Cys-Leu-Pro-Glu-
Ala-Asn-Leu-Gln-Leu-Pro-Asp-Trp-Thr-Glu-Cys-Glu-
Leu-Ser-Gly-Tyr-Gly-Lys-His-Lys-Ser-Ser-Ser-Pro-
Phe-Tyr-Ser-Glu-Gln-Leu-Lys-Glu-Gly-His-Val-Arg-
Leu-Tyr-Pro-Ser-Ser-Arg-Cys-Thr-Ser-Lys-Phe-Leu-
Phe-Asn-Lys-Thr-Val-Thr-Lys-Asn-Met-Leu-Cys-Ala-
Gly-Asp-Thr-Arg-Ser-Gly-Glu-Ile-His-Pro-Asn-Val-
His-Asp-Ala-Cys-Gln-Gly-Asp-Ser-Gly-Gly-Pro-Leu-
Val-Cys-Met-Asn-Asp-Asn-His-Met-Thr-Leu-Leu-Gly-
Ile-Ile-Ser-Trp-Gly-Val-Gly-Cys-Gly-Glu-Lys-Asp-
Ile-Pro-Gly-Val-Tyr-Thr-Lys-Val-Thr-Asn-Tyr-Leu-
Gly-Trp-Ile-Arg-Asp-Asn-Met-Arg-Pro or a glycosylated form, microheterogeneous form or allelic variant thereof.

5. A purified plasminogen activator of claim 2, having the amino acid sequence

Ala-Tyr-Gly-Ser-Cys-Ser-Glu-Leu-Arg-Cys-Phe-Asn-
Gly-Gly-Thr-Cys-Trp-Gln-Ala-Ala-Ser-Phe-Ser-Asp-
Phe-Val-Cys-Gln-Cys-Pro-Lys-Gly-Tyr-Thr-Gly-Lys-
Gln-Cys-Glu-Val-Asp-Thr-His-Ala-Thr-Cys-Tyr-Lys-
Asp-Gln-Gly-Val-Thr-Tyr-Arg-Gly-Thr-Trp-Ser-Thr-
Ser-Glu-Ser-Gly-Ala-Gln-Cys-Ile-Asn-Trp-Asn-Ser-
Asn-Leu-Leu-Thr-Arg-Arg-Thr-Tyr-Asn-Gly-Arg-Arg-
Ser-Asp-Ala-Ile-Thr-Leu-Gly-Leu-Gly-Asn-His-Asn-
Tyr-Cys-Arg-Asn-Pro-Asp-Asn-Asn-Ser-Lys-Pro-Trp-
Cys-Tyr-Val-Ile-Lys-Ala-Ser-Lys-Phe-Ile-Leu-Glu-
Phe-Cys-Ser-Val-Pro-Val-Cys-Ser-Lys-Ala-Thr-Cys-
Gly-Leu-Arg-Lys-Tyr-Lys-Glu-Pro-Gln-Leu-His-Ser-
Thr-Gly-Gly-Leu-Phe-Thr-Asp-Ile-Thr-Ser-His-Pro-
Trp-Gln-Ala-Ala-Ile-Phe-Ala-Gln-Asn-Arg-Arg-Ser-
Ser-Gly-Glu-Arg-Phe-Leu-Cys-Gly-Gly-Ile-Leu-Ile-
Ser-Ser-Cys-Trp-Val-Leu-Thr-Ala-Ala-His-Cys-Phe-
Gln-Glu-Arg-Tyr-Pro-Pro-Gln-His-Leu-Arg-Val-Val-
Leu-Gly-Arg-Thr-Tyr-Arg-Val-Lys-Pro-Gly-Lys-Glu-
Glu-Gln-Thr-Phe-Glu-Val-Glu-Lys-Cys-Ile-Val-His-
Glu-Glu-Phe-Asp-Asp-Asp-Thr-Tyr-Asn-Asn-Asp-Ile-
Ala-Leu-Leu-Gln-Leu-Lys-Ser-Gly-Ser-Pro-Gln-Cys-
Ala-Gln-Glu-Ser-Asp-Ser-Val-Arg-Ala-Ile-Cys-Leu-
Pro-Glu-Ala-Asn-Leu-Gln-Leu-Pro-Asp-Trp-Thr-Glu-
Cys-Glu-Leu-Ser-Gly-Tyr-Gly-Lys-His-Lys-Ser-Ser-
Ser-Pro-Phe-Tyr-Ser-Glu-Gln-Leu-Lys-Glu-Gly-His-
Val-Arg-Leu-Tyr-Pro-Ser-Ser-Arg-Cys-Thr-Ser-Lys-
Phe-Leu-Phe-Asn-Lys-Thr-Val-Thr-Lys-Asn-Met-Leu-
Cys-Ala-Gly-Asp-Thr-Arg-Ser-Gly-Glu-Ile-His-Pro-
Asn-Val-His-Asp-Ala-Cys-Gln-Gly-Asp-Ser-Gly-Gly-
Pro-Leu-Val-Cys-Met-Asn-Asp-Asn-His-Met-Thr-Leu-
Leu-Gly-Ile-Ile-Ser-Trp-Gly-Val-Gly-Cys-Gly-Glu-
Lys-Asp-Ile-Pro-Gly-Val-Tyr-Thr-Lys-Val-Thr-Asn-
Tyr-Leu-Gly-Trp-Ile-Arg-Asp-Asn-Met-Arg-Pro or a glycosylated form, microheterogeneous form or allelic variant thereof.

6. A pharmaceutical preparation comprising a plasminogen activator of claim 2 and a pharmaceutically acceptable excipient.

7. An isolated DNA molecule encoding a polypeptide having the amino acid sequence of a plasminogen activator of claim 2.

8. An isolated DNA molecule encoding a polypeptide having the amino acid sequence of a plasminogen activator of claim 3.

9. An isolated DNA molecule encoding a polypeptide having the amino acid sequence of a plasminogen activator of claim 4.

10. An isolated DNA molecule encoding a polypeptide having the amino acid sequence of a plasminogen activator of claim 5.

11. A vector comprising a DNA molecule of claim 7.

12. A vector comprising a DNA molecule of claim 8.

13. A vector comprising a DNA molecule of claim 9.

14. A vector comprising a DNA molecule of claim 10.

15. A vector of claim 11, capable of expressing a plasminogen activator in a suitable host cell.

16. A vector of claim 12, capable of expressing a plasminogen activator in a suitable host cell.

17. A vector of claim 13, capable of expressing a plasminogen activator in a suitable host cell.

18. A vector of claim 14, capable of expressing a plasminogen activator in a suitable host cell.

19. A host cell, derived from a cell which does not contain an endogenous gene capable of expressing a plasminogen activator, transformed with a vector of claim 15.

20. A host cell, derived from a cell which does not contain an endogenous gene capable of expressing a plasminogen activator, transformed with a vector of claim 16.

21. A host cell, derived from a cell which does not contain an endogenous gene capable of expressing a plasminogen activator, transformed with a vector of claim 17.

22. A host cell, derived from a cell which does not contain an endogenous gene capable of expressing a plasminogen activator, transformed with a vector of claim 18.

23. A method of producing a plasminogen activator, comprising expressing a vector of claim 15 in a suitable host cell, and isolating the thus-produced plasminogen activator.

24. A method of producing a plasminogen activator, comprising expressing a vector of claim 16 in a suitable host cell, and isolating the thus-produced plasminogen activator.

25. A method of producing a plasminogen activator, comprising expressing a vector of claim 17 in a suitable host cell, and isolating the thus-produced plasminogen activator.

26. A method of producing a plasminogen activator, comprising expressing a vector of claim 18 in a suitable host cell, and isolating the thus-produced plasminogen activator.

27. An isolated DNA molecule of claim 8 having the DNA sequence shown in FIG. 8*a* of Bat-PA(L).

28. An isolated DNA molecule of claim 9 having the DNA sequence shown in FIG. 8*a* of Bat-PA(H).

29. An isolated DNA molecule of claim 10 having the DNA sequence shown in FIG. 8*a* of Bat-PA(I).

30. An isolated DNA molecule having the DNA sequence shown in FIG. 8*a*.

31. A method of inducing a thrombolytic effect, comprising administering to a patient in need of such treatment an effective amount of a plasminogen activator of claim 1.

32. A method of inducing a thrombolytic effect, comprising administering to a patient in need of such treatment an effective amount of a plasminogen activator of claim 3.

33. A method of inducing a thrombolytic effect, comprising administering to a patient in need of such treatment an effective amount of a plasminogen activator of claim 4.

34. A method of inducing a thrombolytic effect, comprising administering to a patient in need of such treatment an effective amount of a plasminogen activator of claim 5.

35. A method of claim 31, wherein the patient has suffered a heart attack.

36. A method of claim 32, wherein the patient has suffered a heart attack.

37. A method of claim 33, wherein the patient has suffered a heart attack.

38. A method of claim 34, wherein the patient has suffered a heart attack.

* * * * *